United States Patent [19]

Nohmi et al.

[11] 4,399,035
[45] Aug. 16, 1983

[54] POLYVINYLIDENE FLUORIDE TYPE RESIN HOLLOW FILAMENT MICROFILTER AND PROCESS FOR PRODUCING THE SAME

[75] Inventors: Takashi Nohmi, Fuji; Takao Yamada, Kawasaki, both of Japan

[73] Assignee: Asahi Kasei Kogyo Kabushiki Kaisha, Osaka, Japan

[21] Appl. No.: 276,366

[22] PCT Filed: May 13, 1980

[86] PCT No.: PCT/JP80/00102

§ 371 Date: Jun. 15, 1981

§ 102(e) Date: Jun. 15, 1981

[87] PCT Pub. No.: WO81/00969

PCT Pub. Date: Apr. 16, 1981

[30] Foreign Application Priority Data

Oct. 15, 1079 [JP] Japan .............................. 54-132739

[51] Int. Cl.³ .............................................. B01D 31/00
[52] U.S. Cl. .................................................. 210/500.2
[58] Field of Search .................... 210/500.2, 653, 654, 210/655; 264/178 F, 184, 185, 199, 200; 55/158

[56] References Cited

U.S. PATENT DOCUMENTS

| 3,423,491 | 1/1969 | McLain et al. .................. 210/321.1 |
| 3,615,024 | 10/1971 | Michaels ..................... 210/500.2 X |
| 3,642,668 | 2/1972 | Bailey et al. .................... 260/2.5 M |
| 3,852,224 | 12/1974 | Bridgeford ..................... 260/2.5 M |
| 3,975,478 | 8/1976 | Leonard ...................... 210/500.2 X |
| 4,181,694 | 1/1980 | Hashino et al. ............. 210/500.2 X |
| 4,203,847 | 5/1980 | Grandine ....................... 210/500.2 |
| 4,203,848 | 5/1980 | Grandine ....................... 210/500.2 |
| 4,268,279 | 5/1981 | Shindo et al. ..................... 55/158 X |

FOREIGN PATENT DOCUMENTS

| 48-12871 | 2/1973 | Japan ............................. 210/500.2 |
| 54-11971 | 1/1979 | Japan ............................. 210/500.2 |
| 54-103788 | 8/1979 | Japan ............................. 210/500.2 |
| 1552942 | 9/1979 | United Kingdom ............ 210/500.2 |

Primary Examiner—Frank A. Spear, Jr.
Attorney, Agent, or Firm—Finnegan, Henderson, Farabow, Garrett & Dunner

[57] ABSTRACT

A screen type hollow filament microfilter made of a polyvinylidene fluoride type resin and having a layer structure of two kinds of layers with the support layer and the internal and external skin layers having an easily-controllable and wide average effective pore diameter of 0.05 to 1.0 μm, characterized by having a high selectivity in permeation, a high permeability, a high porosity, an excellent mechanical strength and an excellent chemical resistance and an excellent inertness to living bodies. The microfilter, which has a number of excellent performances, can be produced by extruding a spinning solution comprising a polyvinylidene fluoride type resin, a solvent therefor and at least one kind of surfactant from an annular hollow filament spinning orifice and coagulating the extrudate by using coagulating liquids.

4 Claims, 10 Drawing Figures

FIG.3-(1)
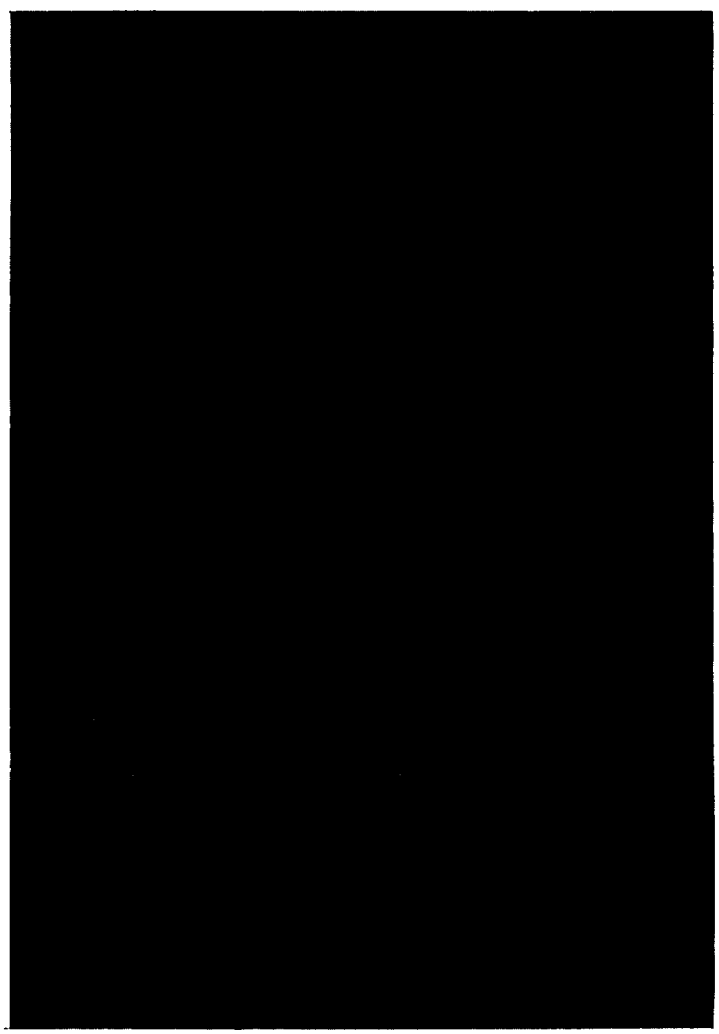

FIG.3-(2)
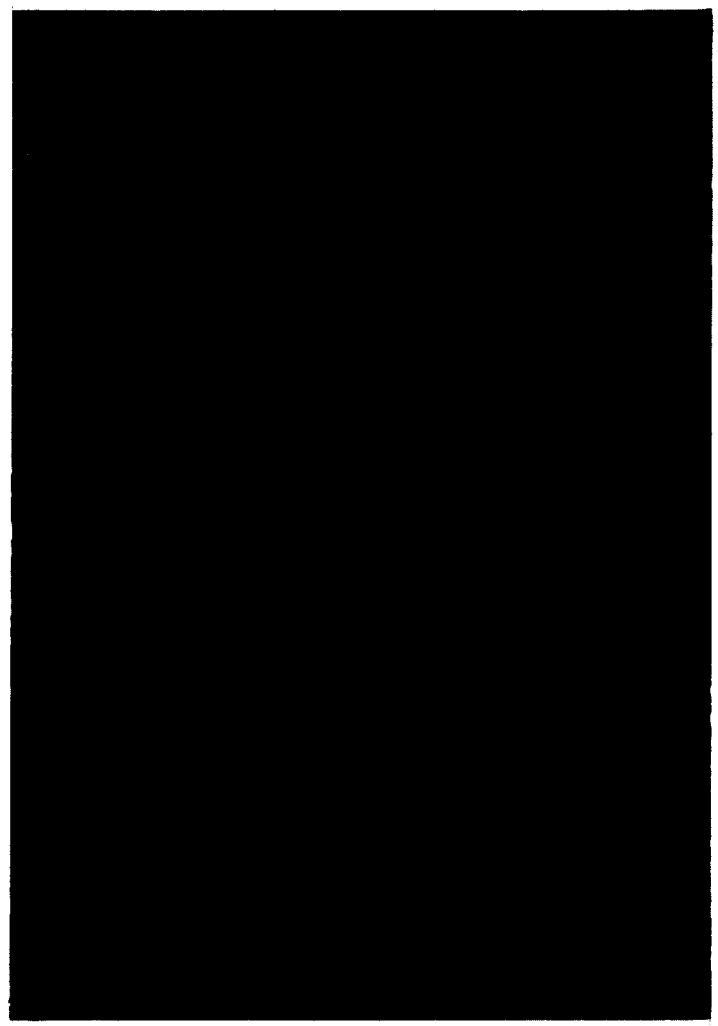

FIG.5-(1)

FIG. 5-(2)

POLYVINYLIDENE FLUORIDE TYPE RESIN HOLLOW FILAMENT MICROFILTER AND PROCESS FOR PRODUCING THE SAME

FIELD OF THE INVENTION

This invention relates to a screen type polyvinylidene fluoride type resin hollow filament microfilter with a double layer structure of skin layers and a support layer. More particularly, the present invention is concerned with a high-performance screen type polyvinylidene fluoride type resin hollow filament microfilter which is capable of separating substances through thin skin layers present on the surfaces of the hollow filament, said thin skin layers comprising pores with a sharp pore diameter distribution, and which has excellent properties such as a high selectivity in permeation, a high permeability, a high porosity, a resistance to repeated drying operations, and is excellent in mechanical strength, chemical resistance, heat resistance, microorganism resistance and inertness to a living body.

DESCRIPTION OF THE PRIOR ART

Recently, using various kinds of materials, there are produced high polymer porous membranes having pore diameters varied in a wide range, for example, reverse osmosis membrane, ultrafiltration membrane, microfilter and the like. Such porous membranes made of these various kinds of materials, due to their excellent properties such as a high permeation selectivity (cut-off characteristics) and a high permeability, have been used in a wide variety of applications, for example; (1) production of plain water from salt water, desaltation of sea water, removal of alkalis, acids and the like from the industrial wastes, (2) recovery of the degreasing solution used in the pretreatment for plating, electrodeposition coating solution and the like, paper-pulp waste water treatment, oil-water separation, oil-emulsion separation, and the like, (3) separation and purification of fermentation products, condensation of fruit juice and vegetable juice, soybean treatment, and separation and purification of products in the food industry such as sugar manufacture and the like, and (4) medical applications such as a filtration type artificial kidney, a microfilter for separating various microorganisms, separation and purification of pharmaceutical products, and the like.

The term "microfilter" is used herein to mean a separator membrane having pores of 0.05 to 1.0 $\mu$m in average pore diameter (2r̄) as is generally defined for its meaning. Such a microfilter is capable of passing therethrough proteins having a molecular weight ranging from thousands to hundreds of thousands, but does not pass therethrough substances with molecular weights larger than the above-mentioned, such as yeast (of 2-4 $\mu$m), fungi (of 1-2 $\mu$m), and causative viruses of diseases (of molecular weight: 2,400,000). Albumin contained in body fluids can pass through it while fungi cannot pass. Emulsion particles cannot pass through it while colloidal particles can pass. Microfilters have been used for separating emulsions, yeasts, fungi and the like. According to the recent remarkable development of applications, the need of use of microfilters under rigorous conditions has been rapidly increased. Such uses include (1) treatment of strong alkali or acid solutions, (2) treatment under high temperatures, (3) treatment of organic solvents, heat sterilization at 121° C. and 1.5 atm in an autoclave, sterilization with hypochlorous acid, and the like. It has, therefore, a strong desire to develop a high-performance microfilter having acid resistance, alkali resistance, heat resistance, solvent resistance and chemicals resistance so that it can withstand the above-mentioned treatments under the rigorous conditions.

With respect to porous membranes produced in the recent development of membrane-producing techniques and the chemicals resistance of such membranes, attention may be called to, for example, a cellulose acetate porous membrane as disclosed in U.S. Pat. No. 3,883,626, which is produced from a solvent and nonsolvent system comprising cellulose diacetate, acetone, methanol, cyclohexanol and $CaCl_2.2H_2O$. Such a cellulose acetate porous membrane obtained from the above-mentioned system not only has pore diameters adjustable in a wide range as desired but also has excellent characteristics such as a sharp pore diameter distribution, a high permeability and the like. However, the cellulose acetate porous membrane is poor in resistance to solvents, acids and the like, namely, for example, the pH region in which the membrane is usable is 4 to 9. On the other hand, a polyacrylonitrile porous membrane is superior, in resistance to solvents, acids and alkalis, to the cellulose acetate porous membrane, that is, the polyacrylonitrile porous membrane is usable in the pH region of 2 to 10 but it is dissolved or decomposed in the pH region above the above-mentioned range. On the other hand, as an improved membrane of the above-mentioned porous membranes, there has been proposed a polysulfone porous membrane. It is excellent in acid resistance and alkalis resistance as compared with the above-mentioned porous membranes, so that it is usable over the pH range as extremely broad as 1 to 14, and it has an excellent heat resistance of up to 100° C. The polysulfone porous membrane, however, has poor resistance to aromatic hydrocarbon solvents, halogenated hydrocarbon solvents and the like, so that it is unusable for a treating solution containing such solvents therein. Furthermore, when the polysulfone porous membrane is exposed for a long period of time to a surfactant that may be contained in a treating liquid, it undergoes changes such as the lowering of strength and the deformation of membrane. Also in solvents such as alcohols and the like, it is caused to change in the pore diameter thereof. Thus, the membrane performance is instable.

For such reasons, it is seriously desired to develop a porous membrane made of new material which has heat resistance, chemical stability such as chemicals resistance and solvent resistance, and high permeability.

In this respect, a polyvinylidene fluoride type resin has such advantages as follows: (1) it is mechanically strong; (2) it has a good heat stability and hence an excellent heat resistance and withstands the majority of chemicals at 135° C.; (3) it has an excellent resistance to radiation and weather; and (4) not only it is very excellent in solvent resistance, acid resistance and alkali resistance but also it withstands completely halogenated compounds, hydrocarbons, alcohols, organic acids, chlorinated solvents, acids, alkalis and the majority of strong oxidizing agents, reducing agents and salts, and it is a far better material in acid resistance, alkali resistance and solvent resistance than polysulfone or polyethersulfone.

However, since the polyvinylidene fluoride type resin has a small critical surface tension of about 25.0 dynes/cm and hence a hydrophobic nature, it is hard to wet with water, and difficulties have been encountered in producing a porous membrane therefrom. For this reason, there has never been provided a high-performance polyvinylidene fluoride resin hollow filament microfilter having sharp substance-separating characteristics and a high water permeability.

In regards to a conventional technique for producing a hollow filament microfilter, there is disclosed, in the specification of British Patent No. 1,506,785, a hollow fiber which comprises a tubular wall membrane having a network structure with many micropores which are uniform in pore diameter at the active points and provides a porosity of at least 60% for the tubular wall membrane. Such a hollow fiber can be produced from cellulose acetate as the material. However, this hollow filament has the following disadvantages: it has poor resistances to chemicals and heat because cellulose acetate is used as the material; it has a large permeation resistance because the active points are so scattered in the membrane that substances to be separated are obliged to pass thereover many times; it is high in mechanical strength, when wetted, because of the highly hydrophilic nature of the material while it is weak in mechanical strength, when dried, due to the occurrence of contraction thereof; difficulties are encountered in preserving and transporting it in a dry state because the permeability is remarkably decreased by the repetition of wetting and drying; even if it were dried by means of freeze-drying, pinholes would be formed in the hollow filament in the course of transportation because of the weak mechanical strength thereof, and even if it were able to be transported in a freeze-dried state, the original permeability could not be recovered at the time of use thereof.

On the other hand, only processes for producing a flat porous membrane have conventionally been known in the case of a polyvinylidene fluoride type resin, such as disclosed in, for example, Japanese Patent Application Laid-Open Specifications Nos. 52-154862 and 52-11261, which is concerned with a process wherein acetone as the main solvent, a non-solvent and a solvent capable of dissolving or swelling the resin are used for producing the porous membrane. This process may be called a dry membrane-producing process in which a large amount of the acetone is allowed to evaporate in air. However, since the vapor pressure of acetone at ordinary temperatures is high, it is difficult to keep the evaporation rate constant, and since the evaporation heat absorbed in the vicinity of the surfaces of the flat membrane varies unstably, the reproducibility of the performances of the membrane is poor. In the process using the solvent and non-solvent, the range wherein the pore diameters are adjustable is extremely restricted, so that a post-treatment, such as stretching or the like, may have to be carried out in order to produce a porous membrane having large pore diameters.

Japanese Patent Application Laid-Open Specification Nos. 50-35265 and 49-126572 disclose processes of producing a porous membrane wherein a polyvinylidene fluoride type resin is dissolved in slow-drying and fast-drying solvents therefor and the resulting solution is soaked in a non-solvent. In such processes, however, there can only be obtained porous membranes having small pore diameters and porosities, as well as small permeabilities can be obtained.

In the case of a highly crystalline fluorocarbon resin as used in Japanese Patent Publications Nos. 51-40099, 47-44341 and 48-8740, the resulting porous membrane needs a support therefor because of its low mechanical strength, and its poor permeability. Furthermore, in preparing the membrane, difficulties are encountered in controlling pore diameters. Thus, the porous membrane can not be of high-performance.

As described hereinbefore, according to the techniques of producing porous membranes using a polyvinylidene fluoride type resin, a satisfactory microfilter, even in the form of a flat membrane, has not been able to be obtained, much less a microfilter in the form of a hollow filament.

There will now be described differences in production techniques between a flat membrane and a hollow filament. There have heretofore been established techniques for producing a flat porous membrane by using any one of various kinds of materials such as polyacrylonitrile, cellulose acetate, polyvinyl chloride, polysulfone, nylon and polyester. However, even in the membrane-producing systems involved in those techniques, few systems are known to have a widely adjustable range for pore diameters to produce a microfilter membrane. In the case of the production of a hollow filament microfilter membrane, further restrictions are imposed because the pore diameters of the porous membrane obtained are much smaller than those in the case of a flat membrane. In the technical viewpoint, it is very difficult for a hollow filament to have pores large in diameter. Furthermore, in the preparation of a hollow filament, an adjustable range for pore diameters is very narrow.

For example, with regards to a system as disclosed in the aforementioned U.S. Pat. No. 3,883,626 which comprises cellulose diacetate, acetone, methanol, cyclohexanol and $CaCl_2.2H_2O$, in the case of a flat membrane prepared therefrom, the pore diameters thereof can be adjusted in the range of from about 100 Å to about 10 $\mu$m, while in the case of a hollow filament prepared therefrom, the upper limit in the adjustable range for pore diameters is only 0.2 $\mu$m. Similarly, in the case of a hollow filament prepared from polyvinyl alcohol, the pore diameters are small and the permeability is poor as compared with the flat membrane.

A great difference in the adjustable range for pore diameters between a hollow filament and a flat membrane is attributed to the following difference in membrane-producing techniques: (i) in the case of the flat membrane, the solvent-evaporation time in air after the casting of a solution for producing the membrane on a glass plate can be adjusted while in the case of the hollow filament, the longest spontaneous falling time of a spinning solution from a spinning nozzle to the surface of a coagulating liquid is 10 seconds which, therefore, is the longest solvent-evaporating time; (ii) in the case of the flat membrane, since in a coagulating bath the coagulating liquid penetrates only from one side of the casted membrane, and since, it takes a long time for the coagulating liquid to diffuse from the surface of the membrane into the inside thereof thereby to form a greatly unsymmetrical structure in the membrane, while, in the case of the hollow filament, since the coagulating liquids penetrate from both the internal and the external surfaces of the membrane, the coagulation occurs rapidly and the phase separation is insufficient; (iii) in the case of the flat membrane, the thickness thereof can be adjusted as desired, while in the case of the hollow filament, too large or too small a thickness thereof results in difficulties in forming an annular shape of the membrane in cross-section; (iv) in the case of the flat membrane, the solvent concentration of the coagulating liquid can be controlled as desired, while in the case of the hollow filament, the solvent concentration of the external coagulating liquid can be controlled but difficulties are encountered in controlling the solvent concentration of the internal coagulating liquid because the quantity of the internal coagulating liquid is limited by the volume of the core hollow portion of the hollow filament, and the solvent concentration of the internal coagulating liquid increases as the migration of the solvent from the membrane into the liquid proceeds; and (v) in the case of the hollow filament, by adjusting the amounts of the spinning solution extruded and the internal coagulating liquid discharged, the shape of the hollow filament in cross-section must be kept annular, while in a flat membrane that is not required. In addition, the production of the hollow filament involves the following problems: (vi) viscosity adjustment of a solution for producing a membrane in which a higher viscosity is preferred since the shape of hollow filament cannot be maintained in too low a viscosity; (vii) choice of the orifice diameter of the spinning nozzle and adjustment of the amount of the spinning solution extruded; (viii) temperature control of the internal and the external coagulating liquids; (ix) temperature control of the solution for producing the membrane; and (x) concentration control of the solution for producing the membrane (a higher concentration such as 15% or more by weight is generally preferred in order to maintaining the shape of the hollow filament because otherwise the membrane is apt to contract and is hardly produced stably). As is apparent from the foregoing, the spinning of a hollow filament porous membrane involves a large number of factors to be controlled as compared with the preparation of a flat membrane, and various conditions in spinning can not be changed independently. Therefore, it is more difficult to adjust the pore diameters in the case of the hollow filament than in the case of the flat membrane.

The technical difficulties have hereinbefore been discussed with respect to the production of a hollow filament porous membrane by the wet spinning process. Generally speaking, four kinds of processes are known for producing a microfilter membrane, they are, (i) wet spinning process, (ii) melt spinning process, (iii) stretch spinning process, and (iv) neutron irradiation spinning process. Hollow filament microfilters obtained from the respective processes have the following disadvantages.

(i) In the case of a hollow filament microfilter prepared from cellulose acetate, polyvinyl alcohol and the like according to the wet spinning process, the pores present on the surface of the hollow filament microfilter do not have circular or substantially circular shapes but have shapes like those of fiber pieces entangled together, those pores being able to be called Up pores which will be explained later.

Up pores increase in size in the thickness direction of a membrane, which has no skin layer in the vicinity of the surface. In this case, whether or not particles can pass through the membrane depends on the narrowest portions (active points) of the pores which constitute passages for the particles in the pores.

In general, porous membranes have Up pores in the surface portions have such disadvantages that they do not have sufficient pressure resistance due to their poor strength, that they become fragile upon drying, that the pore diameters of the membranes decrease remarkably by repeated operations of drying and wetting, and the like. This is so because the membranes do not have sufficient cohesion to the material itself in some portions.

(ii) In the case of a polymer porous membrane produced according to the melt spinning process, which comprises mixing and molding a thermoplastic resin such as a polyolefin with a solvent for the resin, a plasticizer, a filler, a finely divided inorganic powder and the like, followed by a drying or extracting treatment, the membrane has such disadvantages as a low tensile strength, a low burst strength, a small elongation and a high fragility because of the insufficient resin fusion bonding. Furthermore, the porous membrane not only has a low permeability but also has no skin layer. Thus, it is a depth-type porous membrane in which particles are captured in the thickness direction of the membrane.

(iii) In the case of the production of a polymer porous membrane according to the stretch spinning process, high-speed spinning is possible, but the membrane has such disadvantages as a low porosity, a low permeability, elliptical shapes of pores and a broad pore diameter distribution.

(iv) A porous membrane produced according to the neutron irradiation spinning process has such disadvantages as a small number of pores, a low porosity, a low permeability and a high tendency of pore clogging.

Of the above-mentioned four kinds of processes, where the average pore diameters are the same, the wet spinning process can provide a membrane having the highest permeability.

A polyvinylidene fluoride type resin has a critical surface tension of 25 dynes/cm, and is one of the most hydrophobic polymer materials. It's solution is also water-repellent. Therefore, when the water-repellent polymer solution is cast into a liquid with a largely different surface tension such as water, it takes a long time to effect replacement of the solvent with the non-solvent. Therefore, it is next to impossible to spin a hollow filament by the wet spinning process. In fact, such an attempt has never been made, not to mention attempts to spin a polyvinylidene fluoride type resin hollow filament microfilter having a large pore diameter and a high permeability.

For reference, in Table I-(1) and Table I-(2) are listed data on critical surface tensions of various kinds of polymer materials, whether solvents for the polymer materials are present or not and surface tensions of coagulating liquids.

TABLE I-(1)

| Critical Surface Tensions of Various Kinds of Polymers | | |
|---|---|---|
| Polymer Material | Critical Surface Tension γc(dynes/cm) | Solvent |
| polyacrylonitrile | 44 | present |
| polysulfone | 41 | present |
| polyphenylene oxide | 41 | present |
| polystyrene | 33 | present |
| polyethylene | 31 | not present |
| polypropylene | 29 | not present |
| polyvinylidene fluoride | 25-28.5 | present |
| polyfluoroethylene | 22 | not present |
| Teflon | 18.5 | not present |

TABLE I-(2)

| Surface Tensions (γ) of Various Kinds of Liquids Used as Coagulating Liquid | |
|---|---|
| Liquid | Surface Tension (dynes/cm) |
| water | 72.0 |
| dioxane | 33.5 |

TABLE 1-(2)-continued

| Surface Tensions (γ) of Various Kinds of Liquids Used as Coagulating Liquid | |
|---|---|
| Liquid | Surface Tension (dynes/cm) |
| methanol | 22.5 |
| ethanol | 22.3 |
| 1-propanol | 23.7 |
| acetone | 23.3 |

As is apparent from Table 1-(1) and Table 1-(2), a polyvinylidene fluoride type resin is, among various kinds of polymers, one of the resins having the lowest critical surface tension, and has the lowest critical surface tension among the resins having any solvents therefor, wherefrom a hollow filament can be produced by the wet spinning process or the dry spinning process.

The low critical surface tension of the polyvinylidene fluoride type resin indicates that the resin does not yet wet at all with liquids like water having a high surface tension, just as water and oil do not mix. For this reason, no attempts have been made to form a uniform hollow filament porous membrane from a solution of said resin by the wet spinning process.

The present inventors, keeping the above situations in mind, have made investigations on the spinning of a polyvinylidene fluoride type resin solution by means of a hollow filament spinning nozzle by using water as coagulating liquids. A hollow filament obtained in the first stage of the investigations has thick non-porous skin layers formed in the internal and external surface portions, so that the hollow filament did not substantially have any permeability. This may be attributed to slow diffusion of water into the said resin solution because of the formation of an interface between the water and the spinning solution. However, unexpectedly, the electron microscopic photograph of the cross-section of the hollow filament has showed that uniformly formed macropores are present in the interior of the membrane of the hollow filament. This unexpected discovery has led to the completion of the present invention as will be discribed in detail later.

FIG. 1 shows a scanning type electron microscopic photograph of thick skin layers and a support layer comprising macropores in the interior of the membrane of a hollow filament which was produced by spinning a 22.5 wt % dimethylacetamide solution of a polyvinylidene fluoride type resin using water as coagulating liquids. The thick skin layers (k) have no pores and, hence, are non-permeable while the support layer (p) is a porous layer comprising a network structure with large pores in the order of microns in size. The network structure in the interior of the membrane of this polyvinylidene fluoride type resin hollow filament is made up of the pores having an average pore diameter of approximately 1 μm or more. Such large pores can not be found in other hollow filament porous membranes. It is further to be noted that most of the pores are Cp pores, which have not been changed to Up pores. The "Cp" designates "circular pore" while the "Up" designates a pore having a shape other than the circular shape. The formation of the Cp pores in the interior of the membrane of the above-mentioned hollow filament is attributed to the water repellency of the polymer which prevents the penetration of water to the inside of the membrane and the inversion of an islands-in-sea structure initially formed inside the membrane even if a large amount of water flows into the membrane. In the case of Cp pores, the porous membrane is characterized by having a high membrane strength due to the high cohesion of the polymer over all the membrane.

Circular pores called Cp pores result, as will be described in detail later, from a water-in-oil type structure comprising a coagulating liquid phase floating in polymer-rich solution (the oil in the above-mentioned structure corresponds to the polymer-rich phase and the water corresponds to the coagulating liquid) with the advance of desolvation accompanying the shrinkage of the polymer-rich phase by the action of uniform contraction in every direction. On the contrary, Cp pores cannot be formed from an oil-in-water type structure formed by the inversion of a polymer-rich phase.

In spite of such an interior structure, the polyvinylidene fluoride type resin hollow filament does not have substantial permeability because the hollow filament has water-impermeable skin layers in the internal and external surface portions.

The Cp and Up pores will now be explained below [see Kamiide, Manabe, Matsui, Sakamoto and Kajita, "Kobunshi Ronbunshu", Vol. 34, No. 3, pp. 205-216 (1977)]. In general, wet and dry porous membrane-producing processes are classified into two groups based on pore-forming mechanisms, one of which is a pore-forming mechanism according to which Cp pores are formed.

According to the Cp pore-forming mechanism, a solution of one homogeneous phase, when casted, is subjected to phase separation with the advance of the evaporation of the solvent or the penetration of a non-solvent thereinto. Such phase separation first occurs in the surface layer, wherein polymer-lean phases and polymer-rich phases are formed. For example, during the course of producing a flat ultrafiltration membrane by using a spinning solution comprising hydrophilic cellulose acetate, acetone, methanol, cyclohexanol and calcium chloride dihydrate, the concentrated polymer phases are dispersed in the form of fine particles having an diameter of 500 A or less. These particles then aggregate, and they grow into large aggregates and are slowly rendered membraneous. In the above-mentioned spinning solution system, part of the concentrated polymer phases grow into particles as large as about 2 μm in diameter, and most of the particles then begin from the surfaces to aggregate and coagulation-fuse to form the membranes, whereupon the inversion of the polymer-rich phases and the polymer-lean phases occurs, so that the particles of the polymer-rich phases present in the surface layers are connected together to form a structure resembling the islands of the polymer-lean phases floating in the sea of the polymer-rich phase. This is demonstrated in FIG. 2, (a) Cp, the steps 4 and 5. FIG. 2 is a schematic diagram showing the mechanism of formation of a polymer membrane and separately illustrating the formation of Cp pores and the formation of Up pores.

On the other hand, the polymer-lean phases formed by the above-mentioned phase separation have a lower cellulose acetate concentration, higher metanol and cyclohexanol concentrations and a lower salt (CaCl$_2$.2-H$_2$O) concentration than the spinning solution system have before the phase separation. When the polymer-lean phases mix with the solution not subjected to the phase separation and being present in the lower layers adjacent to the surface layers consisting of said polymer-lean phases and the polymer-rich phases, the resulting mixture comes to have a composition capable of bringing about phase separation. Thus, it can be expected that the phase separation of the spinning solution contacted with the layer subjected to the phase separation and being present near the surface progresses consecutively from the surface to the inside. After the concentrated polymer phases fuse in the form of a membrane, the concentrated polymer phase is interconnected surrounding the polymer-lean phases due to the action of surface tension, as shown in FIG. 2, (a), the step 5. Even after the phase separation, the volumes of the polymer-rich and the polymer-lean phases decrease with the evaporation of the solvent, leading to the contraction of fused portions, the decrease in volume of the concentrated polymer phases and the enlargement of the pore diameters. As the fused portions are further contracted, the diluted polymer phase is interconnected in the case of the wet process while in the dry process, bubble-like empty pores are formed. Pores are formed in the portions of the polymer-leans phases or the empty pores by such a procedure of either evaporation or washing of the resulting membrane with water or methanol that the solution of the diluted phases and the solvent, the non-solvent and the additives such as methanol and cyclohexanol in the concentrated phases are removed.

On the other hand, in the case of Up pores, during the course of the phase separation of a homogeneous solution occuring from the surface thereof, fine particles of polymer-rich phases grow into large particles having a particle diameter of about a few micrometers. Thereafter, a large difference of the case of Up pores from the case of Cp pores can be found at the stage of aggregation and interconnection of the particles. More specifically, when the particles of concentrated polymer phases are caused to fuse, diluted polymer phases are interconnected and are not surrounded by the concentrated phases unlike the case of the Cp pore formation.

Such a difference between the Cp pore formation and the Up pore formation is believed to be attributable to a difference in composition of solution at the stage of the phase separation. According to the Up pore formation mechanism the lower the polymer concentration of the concentrated polymer phases the more finely complicated aggregates are formed, and the higher the porosity of and the larger the pore diameter of the membrane. In the case of the Up pores thus formed, the continuous phase of the polymer consists of the aggregates of the fine particles. Therefore, some fine polymer particles are found not to participate in the formation of the porous membrane, and the pores of the porous membrane do not have substantially circular shapes but assume something like fiber pieces entangled together. Furthermore, in the case of the Up pores, the polymer-rich phases correspond to the "islands" in the above-mentioned "islands-in-sea" structure, so that islands not contacted with adjacent islands during the course of membrane formation precipitate as fine polymer particles, which can be observed by means of an electron microscope. On the other hand, in the case of the Cp pores, the polymer concentration of the body of the membrane is reduced, and macrovoids develop in the radial direction of the filament for making up for the reduction. Furthermore, the greatest characteristic differences between Up pores and Cp pores can be found in pore diameter. More specifically, a microfilter with an average pore diameter ($2\bar{r}$) of 0.05 $\mu$m or more produced by the wet process has Up pores, while an ultra- filtration membrane with an average pore diameter ($2\bar{r}$) of less than 0.05 $\mu$m has Cp pores.

However, a microfilter with an average pore diameter ($2\bar{r}$) of 0.05 $\mu$m or more produced by the conventional wet process comprises Up pores and, hence, has a poor mechanical strength. Furthermore, the microfilter is not sharp in pore diameter distribution and, hence, is poor in permeation selectivity. Therefore, various difficulties have been experienced in using the microfilter in a practical sense. In view of the above, it has been strongly desired in the art to develop a hollow filament microfilter which has advantages in practical use, particularly, a high efficiency of treating substances and a high mechanical strength. Accordingly, it is an object of the present invention to provide a hollow filament microfilter which has a high permeation selectivity, a high permeability, a resistance to repeated drying, a high mechanical strength, an excellent heat resistance, an excellent chemicals resistance, and a high inertness to living body. It is another object of the present invention to provide a process for preparing, without difficulties, a hollow filament microfilter having the above-mentioned performances.

DISCLOSURE OF THE PRESENT INVENTION

The structure of a polyvinylidene fluoride type resin porous membrane hollow filament according to the present invention will now be described from the standpoint of the above-mentioned Cp and Up pores. The polyvinylidene fluoride type resin porous membrane hollow filament has the Cp pores in its most parts ranging from the surface to the inside of the membrane, and the average pore diameter ($2\bar{r}$) of the Cp pores is in the range of from 0.05 $\mu$m to 1 $\mu$m. Furthermore, in many cases, there are found voids having large pore diameters which are characteristic of the Cp pores. FIG. 3-(1) is a scanning type electron microscopic photograph ($\times$12000 magnification) which shows the Cp pores in the inner surfaces of macrovoids of the polyvinylidene fluoride resin type hollow filament microfilter according to the present invention. FIG. 3-(2) is a scanning type electron microscopic photograph ($\times$12000 magnification) which shows the Cp pores formed in the external skin layer surface of the same hollow filament. Cp pores cannot be obtained even when a hollow filament microfilter is formed from a hydrophilic polymer. Therefore, it is quite surprising that a hollow filament microfilter having Cp pores inside should be prepared from a polyvinylidene fluoride type resin which material has, heretofore, been considered unsuitable for producing porous membranes.

The formation of Cp pores would be attributable, as described above to such a mechanism that, due to the water-repellent nature of a polyvinylidene fluoride type resin solution, an interface is formed between a coagulating liquid and the polyvinylidene fluoride type resin solution, which then gells to form skin layers, and the resulting ski layers prevent the penetration of excess water into the hollow filament, thereby accelerating formation of a continuous phase of the polymer.

The pore formation mechanism of a polyvinylidene fluoride type resin porous membrane will be summarized as follows.

When a hollow filament is spun by using, for example, a dimethylacetamide (hereinafter abbreviated as DMAc) solution of a polyvinylidene fluoride type resin and water as coagulating liquids, an interface is formed between the polyvinylidene fluoride type resin solution and the coagulating liquids, and then phase separation occurs in the interface. As a result of the phase separation, polymer-rich phases and a polymer-lean phase are formed, and the polymer-rich phases are connected together to form a continuous polymer phase, which turns into a skin layer on gelation of the polymer.

When a polyvinylidene fluoride type resin solution is used, water penetrates into the polymer-lean phase cannot diffuse rapidly inside the membrane of the hollow filament because of the interference of the hydrophobic and continuous polymer-rich phase but diffuses so slowly inside the membrane of the hollow filament that the micro-phase separation develops uniformly inside the membrane of the hollow filament.

FIG. 4 is a scanning type electron microscopic photograph ($\times 420$ magnification) showing a freeze-broken section of a hollow filament microfilter according to the present invention. FIG. 5-(2) is an enlarged photograph ($\times 1200$ magnification) of a uniform (macro-pores) network structure found over the central support layer portion of the microfilter. It is apparent from these photographs that the polyvinylidene fluoride type resin porous membrane hollow filament has a very uniform internal structure comprising Cp pores.

On the other hand, in the case of common porous membranes having Cp pores, for example, a hollow filament ultrafiltration membrane formed from polyacrylonitrile or polysulfone the diameters of the pores of the support layer increase towards the inside of the membrane, and reach maximum values at an equidistant point from both the surfaces of the membrane.

As compared with the formation of the skin layers, the formation of the uniform structure inside the membrane of the hollow filament takes a long time, and, during that time, and prior to gelation the micro-phase separation well develops, so that the pore structure of the microfilter formed has a low permeation resistance and allows, for example, water to pass freely therethrough.

Since the Cp pores grow up from the surfaces of the filament during the formation of the polyvinylidene fluoride type resin hollow filament structure, all the polymer used takes part in the formation of the pore structure. Therefore, in this case, there is no precipitation at all of fine particles of the polymer, as opposed to the case where Up pores grow up from the surface of the membrane. Accordingly, the resulting polyvinylidene fluoride type resin hollow filament microfilter has an excellent pressure resistance.

By contrast, in the case of common microfilters having Up pores, the pores in the surface portions thereof do not have circular shapes, and part of the polymer used turns into fine spherical particles, which, without bonding to the other particles to contribute to the formation of the membrane, flow away from the surfaces of the membrane into the coagulating liquid and/or are stuck in the network during the course of the pore formation. The membrane as mentioned above has a poor mechanical strength and a poor pressure resistance.

The foregoing illustrates the poor formation mechanism in the preparation of a hollow filament by using a DMAc solution of a polyvinylidene fluoride type resin and water. The most knotty problem in this case, as mentioned above, is the formation of a non-porous skin layer which completely prevents the transmission of water therethrough. Because of such a thick skin layer, a membrane, as obtained by casting a DMAc solution of a polyvinylidene fluoride type resin into water, is water-impermeable.

The present inventors conceived that, if only pores could be formed, as desired, in the skin layers present on the surfaces of the above-obtained hollow filament, a screen-type hollow filament microfilter having a greater strength and a higher permeability than those of the conventional microfilters could be developed in view of the fact that the above-obtained hollow filament has highly permeable Cp pores in its support layer.

With a view to finding a pore-forming agent which, without preventing the growth of the Cp pores in the support layer of the membrane, can form pores having pore diameters adjustable as desired, the present inventors have made extensive and intensive investigations. As a result, it has been surprisingly found that, by adding a surfactant(s) to a spinning solution, pores having been controlled, as desired, with respect to their pore diameters and can be formed in the skin layer of a water-repellent polyvinylidene type resin hollow filament. Thus a highly permeable hollow filament microfilter has been found which has a layer structure of two kinds of layers with the support layer and the internal and external skin layers. The present invention has been completed based on this novel finding.

More specifically, according to the present invention, there is provided a polyvinylidene fluoride type resin hollow filament microfilter comprising a polyvinylidene fluoride type resin membrane having a substantially annular shape in cross-section and comprising internal and external surface skin layers and a support layers connected thereto; said skin layers being uniformly porous permeable layers with an average pore diameter ($2\bar{r}_s$) of 0.05 to 1.0 $\mu$m, said support layer being a uniformly porous layer with an average pore diameter ($2\bar{r}_a$) of 1 to 10 $\mu$m, a relationship represented by the formula $\bar{r}_a/\bar{r}_s \geq 4$ being satisfied, said resin membrane having an average effective pore diameter ($2\bar{r}$) of 0.05 to 1.0 $\mu$m and a porosity of 60 to 85%.

The hollow filament microfilter of the present invention is very excellent in heat resistance, chemicals resistance, acid resistance and alkali resistance because it is made from a polyvinylidene fluoride type resin, and is also very excellent in mechanical strength, permeability and permeation selectivity due to the mechanism of membrane formation.

The present invention will now be described in detail.

The hollow filament of the present invention has a structure as shown in FIG. 6, which is a schematic sectional view of a hollow filament according to the present invention. As depicted in FIG. 6, the hollow filament of the present invention comprises skin layers 1 constituting the internal and external surface portions of the hollow filament, and a support layer 2 supporting said two skin layers.

The structure of the skin layers is characteristic of the hollow filament of the present invention. The skin layers have a large number of pores of 0.05 to 1.0 $\mu$m in average pore diameter ($2\bar{r}_s$). The size and number of pores present in the skin layer portions and the thickness of the skin layers are determining factors for water permeability and permeation selectivity of a hollow filament. The greater the number of pores, the higher the permeability and the permeation selectivity. A hollow filament having $1 \times 10^7$ to $1 \times 10^{10}$ pores/cm$^2$ can be obtained. The sharper the pore diameter distribution, the higher the permeation selectivity, and the ratio $\bar{r}_{s2}/\bar{r}_{s1}$ is desired to be 1.5 or less, preferably 1.3 or less. In the above, $$\bar{r}_{s2} = \int r_s^2 N(r_s)dr_s / \int r_s N(r_s)dr_s$$

$$\bar{r}_{s1} = \int r_s N(r_s)dr_s / \int N(r_s)dr_s$$

The values of $r_s$ and $N(r_s)dr_s$ are obtained by observing the surface using an electron microscope.

The formation of the structure of the skin layers is ascribed to the water repellency of a polyvinylidene fluoride type resin solution used and to the specific composition of the spinning solution and the preparation process for a hollow filament, both of which are disclosed, for the first time, in the present invention. The average pore diameter (2r) of pores present in the skin layers is considerably large, i.e., between 0.05 μm and 1.0 μm.

The support layer is present contiguously to the internal and external skin layers of the hollow filament. The polymer component of the support layer is identical with that of the skin layers. Pores in the support layer are uniform macropores having an average pore diameter ($2\bar{r}_a$) of 1 to 10 μm. Furthermore, the average pore diameter ($2\bar{r}_s$) of the pores in the skin layers and the average pore diameter ($2\bar{r}_a$) of the macropores in the support layer satisfy a relationship represented by the formula $\bar{r}_a/\bar{r}_s \geq 4$.

In addition to the above-mentioned uniform macropores, the support layer has large macrovoids as shown in FIG. 6-(3). In general, the macrovoids are in forms elongated in a radial direction of the microfilter viewed in cross-section. When a hollow filament microfilter having a membrane thickness of 100 to 500 μm is observed, the macrovoids in the support layer are generally 10 to 200 μm in width or in their lateral axial direction and 20 to 400 μm in length or in their longitudinal axial direction. The terms "longitudinal and lateral axial directions" in the cross-section of a macrovoid are used herein to mean the direction of the maximum size of the macrovoid in a radial direction of the microfilter and the direction of the maximum size of the macrovoid in a direction perpendicular to said radial direction, respectively. In general, the size in a longitudinal axial direction of a macrovoid larger than that in a lateral axial direction thereof. However, in the case where the viscosity of the spinning solution is increased and in the case where the temperature of the coagulating bath and/or the spinning solution is lowered, the size in a lateral axial direction of a macrovoid may, in some cases, be equal to or larger than the size in a longitudinal axial direction thereof because of the delayed completion of coagulation.

However, in general, the maximum lengths in longitudinal axial direction of macrovoids present in the hollow filament microfilter of the present invention have some proportional relationship to the membrane thickness and may usually be at least 10% and at most 80% of the membrane thickness. Therefore, when the membrane thickness is reduced to 100 μm or less, the macrovoids become proportionally small in size, and at the membrane thickness of 50 μm or less the macrovoids cannot be distinguished from the pores present in the support layer.

The presence of macrovoids is characteristic of porous membranes having Cp pores. In the case of the Cp pore formation, as the gellation proceeds to form a support layer, a membrane is formed with the gradual shrinkage of a continuous polymer phase, which causes defects generated by the shortage of the polymer to be expanded to grow into macrovoids. Therefore, the sizes and shapes of macrovoids depend on gelation rate-controlling factors such as the quantity of surfactant(s) in a spinning solution and the concentration of the spinning solution. Such macrovoids are observed only in porous membranes with Cp pores which are formed by the gelation of a continuous polymer phase caused by water-in-oil type microphase separation (oil corresponds to the polymer-rich phase and water corresponds to the coagulating liquid phase). The formation of macrovoids has a short-circuit connecting pore-forming effect and, hence, contributes to an increase in the permeability of the membrane, but does not have an adverse effect on the selectivity of the membrane.

However, when the lengths, in a longitudinal axial direction, of the macrovoids exceed 80% of the membrane thickness, although water permeability of the membrane increases slightly, the mechanical strength, burst strength and the like of the membrane are reduced markedly so that the hollow filament unfavorably tends to easily split or tear longitudinally. Therefore, the hollow filament structure is desired to have larger macrovoides having a length in a longitudinal axial direction of at most 80%, more preferably at most 70%, of the membrane thickness. Burst strength is expressed by a pressure at which, when a wet hollow filament is cut to 20 cm in length and compressed air is introduced into the cut hollow filament from both the sides thereof at the flow rate of 1 kg/cm²/min, the hollow filament ruptures.

In order to secure a high permeability for even a membrane having a thickness of 50 μm or more, the presence of macrovoids in the hollow filament structure is preferred. Since the polyvinylidene fluoride type resin material is hydrophobic and the Cp pores are progressively formed at the time of gelation, there are formed macrovoids, which lead to a unique structure as cannot be found in other microfilters.

The support layer is thick as compared with the skin layers and the thickness of the support layer is at least 10 times that of the skin layers.

The average effective pore diameter ($2\bar{r}$) of the hollow filament of the present invention comprising the skin layers and the support layer is in the range of 0.05 μm to 1.0 μm. This will be the matter of course since the pore diameter in skin layers on which the permeability of the membrane will depend is small.

The average effective pore diameter ($2\bar{r}$) is defined by the following formula [See Kamiide, Manabe & Matsui: "Kobunshi Ronbunshu" Vol. 34, No. 4, pp. 299–307 (1977)].

$$\bar{r} = \{8Q\eta d/(\Delta P \cdot Pr)\}^{\frac{1}{2}}$$

wherein

Q is the amount per unit area and unit time of a liquid passed through a porous membrane, cm³/cm².sec;

η is the viscosity of the liquid, poises;

d is the thickness of the porous membrane, cm;

ΔP is the pressure difference between a pressure on one surface of and a pressure on the other surface of the porous membrane, dynes/cm²; and Pr is the porosity of the porous membrane, %. The porosity (%) is defined by the following formula.

$$Pr = (1 - \rho b/\rho a) \times 100 \ (\%)$$

wherein

ρa: the density of the porous membrane material having no pores

ρb: the value obtained by dividing the weight of the porous membrane by the volume of the same The porosity of the hollow filament microfilter of the present invention is in the range of 60 to 85%, preferably 65 to 80%. A hollow filament microfilter having a porosity of more than 85% cannot be used because of the poor mechanical strength and the poor burst strength. On the other hand, a hollow filament having a porosity of less than 60% has too low a water permeability to be used as a microfilter.

The average radii of the pores present in the skin layers and the macropores present in the support layer can be calculated, according to the electron microscope method, from the following formula. For example, the $\bar{r}_s$ can be expressed as follows:

$$\bar{r}_s = \int r_s N(r_s) dr_s / \int N(r_s) dr_s$$

wherein $r_s$ is the radius of a pore present in the skin layer; and $N(r_s)$ is a pore radius distribution function defined on the basis that the number of pores having a pore radius falling within the range of from $r_s$ to $r_s + dr_s$ is expressed as $N(r_s)dr_s$.

The value of $\bar{r}_s$ is obtained by observing the pores present in the internal and external wall surfaces of the hollow filament by using the electron microphotograph of the filament and finding a pore radius distribution function for the hollow filament. In the case of a hollow filament obtained using a spinning solution and an internal and an external coagulating liquids having the same component(s), even when the value of $\bar{r}_{sf}$ and the value of $\bar{r}_{sb}$ ($\bar{r}_{sf}$ is the $\bar{r}_s$ in the external surface and $r_{sb}$ is the $\bar{r}_s$ in the internal surface) are calculated, there is generally found the relationship: $\bar{r}_{sb}/\bar{r}_{sf} \approx 1.0$. When the value of $\bar{r}_{sf}$ is largely different from that of $r_{sb}$, the average pore radius ($\bar{r}_s$) in the skin layers is representatively expressed by the formula: $r_s = (\bar{r}_{sf} + \bar{r}_{sb})/2$.

The value of $r_a$ may be determined by finding a pore radium distribution function for $r_a$ by using the electron microphotograph of the cross-section of the hollow filament. However, in order to accurately determine the values of $r_a$, the procedures are followed which comprise embedding the hollow filament in a resin, cutting the resultant to obtain a super-thin cut sample, taking the scanning electron microscopic photograph of the sample and following the same procedure as described above. Macropores tend to increase slightly in radius with the distance thereof from the internal and external surfaces of the hollow filament. In finding the value of $\bar{r}_a$, macropores in a uniform support layer are examined with macrovoids being expected. Pores that can be seen on the surfaces of the macrovoids are the exposed macropores and have substantially the same pore radius as those of the macropores in the support layer. Generally speaking, the uniform support layer is located around the center of the entire support layer and can usually be distinguished from layers in the vicinity of the internal and external surfaces in which layers a number of macrovoids are present.

The skin layers of the hollow filament porous membrane of the present invention play the role of selective filtering layers since they have a small average pore diameter and a sharp pore diameter distribution. They also advantageously enable filtration to be carried out without resistance since they are very thin. The support layer of the hollow filament reinforce the thin skin layers. The support layer does not give any resistance to filtration against a liquid passed through the skin layers because the support layer has macropores with a large average pore diameter as well as macrovoids. Moreover, the microfilter of the present invention has an excellent pressure resistance because the pores in the support layer are the Cp pores. The microfilter of the present invention has extremely excellent resistances to heat and to chemicals, acids and alkalis because its material is a polyvinylidene fluoride type resin.

In the case of hollow filament porous membranes prepared from other materials according to the wet process, when the pores are enlarged from those for the ultrafiltration membrane to those for the microfilter, they change from Cp pores to Up pores. For example, cellulose acetate, polyacrylonitrile, polyether-sulfone, polysulfone, polyvinyl alcohol, polyvinyl chloride and the like are materials from which ultrafiltration membrane can be produced. As the average pore diameter of a membrane produced from any of such materials are increased, Up pores are formed. To the contrary, the polyvinylidene fluoride type resin hollow filament microfilter is characterized in that Cp pores exist stably over a wide range of pore diameters and even in the case of the average pore diameter ($2\bar{r}$) of 0.05 to 1.0 μm.

The stable presence of Cp pores in the polyvinylidene fluoride type resin hollow filament microfilter of the present invention will be confirmed by the formation of Cp pores in the surface of macrovoids and the formation of macrovoids in the support layer.

The special porous membrane structure comprising a combination of the support layer having uniform and large macropores, macrovoids, and skin layers cannot be obtained in the case of other polymer materials even if a macrovoid-forming material such as a viscous liquid, e.g., liquid paraffin or a solid powder, which facilitates the phase separation, is used in the spinning solution.

In other words, the above-mentioned structure is formed only by the combination of a water-repellent polyvinylidene type resin material and a surfactant(s). The above-mentioned structure has never been known which comprises the combination of micropores attributed to the action of the surfactant(s) at the time of formation of the skin layers, and uniform macropores and macrovoids in the support layer attributed to the use of the polyvinylidene fluoride type resin material.

The term "polyvinylidene fluoride type resins" is used herein to include vinylidene fluoride homopolymers; random and block copolymers of vinylidene fluoride such as vinylidene fluoride-tetrafluoroethylene copolymers, vinylidene fluoridepropylene hexafluoride copolymers, and ethylene-ethylene tetrafluoride copolymers; and their mixtures. The term "polyvinylidene fluoride type resns" further includes blend polymers of the above-mentioned polyvinylidene fluoride type polymers with a small quantity of other polymer such as polysulfone, polyether-sulfone, polycarbonate, 6-nylon, 6,6-nylon, cellulose diacetate, polyurethane, other vinyl polymer, polyamide or polyimide; the vinylidene fluoride type polymer content of said blend polymers being 70% or more by weight.

A polyvinylidene fluoride type resin is a fluorine compound having a chemical structure of $(CF_2—CH_2)_m$ (wherein m is a positive integer) and having an average fluoride content of 50 to 60% in one molecule. It is preferred in the present invention that a stable polymer with a high crystallinity in which methyl groups and methyl fluoride groups are bonded alternately be used. A homogeneous spinning solution for producing a membrane which is prepared by mixing such a polymer with a surfactant(s) and a solvent (s) is stable and is not denatured even after allowed to stand for a long time. More preferred resins are such that a mixture comprising 22 wt % of each resin polymer and 20 wt % of polyethylene glycol does not increase in viscosity by more than 15% when allowed to stand at 60° C. for 12 hours. Preferred polyvinylidene fluoride type resins to be used in a spinning solution for preparing a membrane are those having an average molecular weight of $25 \times 10^5$ or more. Examples of such polyvinylidene fluoride type resins include Kynar (tradename of a polyvinylidene fluoride type resin of a grade for solution, product No. 461, manufactured by Pennwalt Company, U.S.A.). A spinning solution prepared from a solution of this polymer is stable and changes little with respect to ints viscosity even after allowed stand for a long time.

Where a highly concentrated solution of a polymer with a 20 wt % or more polymer content is instable when allowed to stand for a long time, a spinning solution of such a polymer is desired to have a low polymer content of 20 wt % or less. The use of such a low polymer content spinning solution for spinning a hollow filament can prevent the denaturation thereof, the clogging of a filter or a nozzle and the lot-to-lot variation of the diameters of the resulting filaments, thereby enabling the hollow filaments to always have desired performance as microfilters. A dispersing solvent medium may be added to the spinning solution.

Any solvent can be used in the preparation of the hollow filament of the present invention as far as it can act as the solvent for a polyvinylidene fluoride type resin. Particularly preferred is a solvent which can dissolve a polyvinylidene fluoride type resin to a concentration of 30 wt % or more at a temperature of 100° C. or less. As such solvent, there can be mentioned, for example, dimethylformamide (DMF), dimethylacetamide (DMAc), diethylformamide (DEF), trimethyl phosphate, diethylacetamide (DEAc), N-methylpyrrolidone (NMP), hexamethylphosphoric triamide (HMPA), tetramethylurea (TMU), and mixed solvents of two or more of the above-mentioned solvents. Those solvents are preferred which lower the crystalline melting point (Tm) of a polyvinylidene fluoride type resin to about 90° C. or less and have a boiling point within the range of about 160° to 210° C., and which can easily dissolve a polyvinylidene fluoride type resin therein to prepare a polymer solution with a concentration of 11 to 30 wt % suitable as a spinning solution for producing a membrane.

A polyvinylidene fluoride type resin solution having a high viscosity may at times undergo gelation when allowed to stand because of the intermolecular cohesion of the polyvinylidene fluoride type resin molecules in the dispersion state. Such gelation can be effectively prevented by lowering the viscosity of a spinning solution for producing a membrane. The viscosity of the spinning solution can be easily lowered by adding a dispersing solvent medium to the spinning solution.

As the dispersing solvent medium advantageously used for the above-mentioned purpose, there are also solvents which are incapable of dissolving a polyvinylidene fluoride type resin to obtain a solution having a resin concentration of 30 wt % or more at a temperature of 100° C. or less, and are capable of being dissolved in a polyvinylidene fluoride type resin solution in any proportions without causing gelation of the solution. Examples of such solvents include poor solvents, such as dimethyl sulfoxide, dimethyl adipate, diethyl oxalate, dimethyl phthalate, diethyl adipate, diethyl succinate, dimethyl succinate and triethyl phosphate, which can dissolve only a small amount of a polyvinylidene fluoride type resin; and solvents, such as dioxane, acetone, cyclohexanol, methyl isobutyl ketone, tetrahydrofuran, methyl ethyl ketone and methyl amyl ketone, which do not have an ability of dissolving a polyvinylidene fluoride type resin but do not decrease the dissolving power of the solvent for the polyvinylidene fluoride type resin, and which can be sufficiently mixed with a polyvinylidene fluoride type resin solution and, hence, can lower the viscosity of the polyvinylidene fluoride type resin solution so that the replacement of the solvent with the coagulating liquids proceeds so smoothly to cause the microphase separation rapidly. Mixtures of two or more of the above-mentioned liquids such as mixtures of dioxane and dimethyl sulfoxide can also be used. Of the above-mentioned dispersing solvent mediums, dioxane, dimethyl sulfoxide and the like having high boiling points are particularly preferred.

By adding one or more of the above-mentioned dispersing solvent mediums to a polyvinylidene fluoride type resin solution, not only the viscosity of the resin solution can be adjusted to be suitable for preparing a membrane, but also stable micro-phase separation can be achieved, and a membrane having a high permeability can be prepared when the dispersing solvent medium is used in combination with a surfactant or surfactants.

The amount of the dispersing solvent medium may be from 1 to 25% by weight based on the total weight of the spinnning solution. By adding a dispersing solvent medium, a stable low viscosity spinning solution for producing a hollow filament can be obtained which does not change in viscosity with the lapse of time and does not undergo gelation. It is not recommended to employ too large an amount of a dispersing solvent medium because the viscosity of a spinning solution for producing a membrane is lowered too much, leading to the difficulty in spinning. Furthermore, as a result of the lowering of the viscosity of the spinning solution, the skin layers present on the surface portions of the resulting hollow filament are thickened and, hence, the water permeability of the hollow filament is markedly lowered as in the case where the polymer concentration of the spinning solution is lowered. For these reasons, the preferred amount of the dispersing solvent medium is from 1 to 25% by weight, more preferably from 1 to 15% by weight based on the total weight of the spinning solution. Furthermore, it is preferred that the total weight of the surfactant(s) and the dispersing solvent medium(s) should not exceed the weight of a polymer employed. In case the above-mentioned total weight exceeds the weight of the polymer, it becomes difficult to obtain a high-performance hollow filament microfilter having a high mechanical strength as well as a high water permeability.

More detailed explanation on the stability of a polyvinylidene fluoride type resin spinning solution will now be made below. For example, the viscosity of a 25 wt % solution of vinylidene fluoride homopolymer in dimethylacetamide is 5,300 poises at 25° C. In the case of addition of a surfactant to a dimethylacetamide solution of polyvinylidene fluoride type resin, for example, when 20 parts (by weight) of a polyvinylidene fluoride type resin, 60 parts of dimethylacetamide, and 20 parts of polyoxyethylene nonylphenol ether as a surfactant (Emulgen 903 manufactured by Kao Atlas Co., Ltd., Japan) are mixed and stirred, the viscosity of the resultant solution is 8,000 poises at 25° C., and increase with the lapse of time, leading to the gelation of the solution after a week. On the other hand, in the case of a solution comprising 20 parts (by weight) of a polyvinylidene fluoride type resin, 40 parts of dimethylacetamide, 20 parts of dioxane and 20 parts of polyoxyethylen nonylphenol ether, the solution has a viscosity of 2,000 poises at 25° C. and the gelation does not occur even after a week. The above facts indicate that the addition of a dispersing solvent medium to a spinning solution further stabilizes the spinning solution, which is stabilized by a surfactant to such an extent that a hollow filament can be spinned, that is, to such an extent that the spinning solution does not exhibit an increase of more than 15% in viscosity even after allowed to stand for 12 hours or more. In this way, dioxane as the dispersing solvent medium stabilizes the spinning solution without any adverse effect on the dissolving power of the solvent for the polyvinylidene fluoride type resin, so that the membrane-forming performance of the spinning solution is remarkably improved.

The term "surfactant" is used herein to mean a substance which exhibits a great surface activity even in a low concentration and which can be adsorbed on a surface or interface. In general, the term "surfactant" indicates an amphiphatic substance having appropriate hydrophilic and lipophilic groups. However, in the present invention, besides common amphiphatic substances, other substances capable of being adsorbed on an interface or surface are also included in the category of "surfactant".

For use as surfactants, any of ampholytic, anionic, cationic and nonionic surfactants may be employed. Preferred are surfactants which are homogeneously soluble in the solvent used for a polyvinylidene fluoride type resin and are stable even under high temperatures. More preferred are surfactants which are homogeneously soluble in the above-mentioned solvent even when the surfactant concentration of the resulting solvent exceeds 10% by weight. Examples of such preferred surfactants are nonionic surfactants such as polyoxyethylene alkyl esters, polyoxyethylene alkylphenol ethers, sorbitan fatty acid esters, polyoxyethylene sorbitan fatty acid esters, polyoxyethylene alkylamine, polyoxyethylene fatty acid esters, glycerin, glycerin fatty acid esters, ethylene glycol, oxyethylenes, e.g. di-, tri- and tetra-ethylene glycols, oxypropylenes, e.g. propylene glycol, di-, tri-, and tetra-propylene glycols, derivatives, and block copolymers of polyoxy-ethylenes and -propylene; anionic surfactants such as alkyl phosphates, polyoxyethylene alkylsulfates, naphthalenesulfonic acid-formalin condensates, salts of fatty acid and sulfuric acid salts of alkyl esters; and cationic surfactants such as alkyl amine salts. In addition to the aforementioned surfactants, there may also be employed, as surfactants in the present invention, polymers such as polyvinyl alcohol and polyvinyl pyrrolidone which show a great adsorbability on interfaces between gases and water, oils and water, and solids and liquids, and which are uniformly soluble in both water and a solvent for a polyvinylidene fuloride type resin. Those compounds to be used as the surfactants may contain builders therein, but a lower builder content is preferred.

It is more effective to use at least two kinds of surfactants than to use one. When using two or more types of surfactants, it is preferred that at least one is a nonionic surfactant. Preferred nonionic surfactants are, those which have alkylene oxide [$+R-O+$] groups or polyalkylene oxide [$-R-O-n$] groups on its main chain or side chains, such as alkylene glycols and polyalkylene glycols having the general formula H—O—R—O—nH (wherein n is a positive integer of one or more and R is an alkyl group). During the formation of the skin layers of the hollow filament, the above-mentioned specific nonionic surfactant forms micro-phases in the "water-in-oil" type structure, comprising the polymer-rich phases and the polymerlean phase, and the other surfactant is adsorbed on the interface between the microphases and their surrounding phase with the hydrophilic groups and hydrophobic groups being oriented in inside and outside directions of the micro-phases. Thus, the micro-phases are stabilized, which markedly expands the pore diameter-adjustable range so that the desired pores can be obtained and that the water permeability can be increased. Furthermore, the use of the above-mentioned nonionic surfactant leads to the following advantages: (1) it is easy to prepare a solution having a proper viscosity for producing a membrane; (2) the spinning solution is stabilized and does not undergo gelation for a long time; (3) even if a large amount of said nonionic surfactant is added, a homogeneous polymer solution can be obtained which does not undergo the micelle-formation; (4) it is easy to mix said nonionic surfactant with other anionic, cationic, ampholytic or nonionic surfactant as desired; (5) said nonionic surfactant can form a stable homogeneous solution even at a temperature as high as 70° to 80° C., and has a good heat resistance, and (6) it is easy to mix said nonionic surfactant with a dispersing solvent medium, a non-solvent and the like.

When two or more kinds of surfactants are used, a larger total amount of the surfactants is preferred. The lower limit of the amount of a surfactant to be added is preferably at least 0.5 percent by weight. By adding surfactants into a polyvinylidene fluoride type resin solution, when said resin solution is immersed in water, the water can penetrate quickly into the boundary polymer solution phase formed between the polymer solution and the coagulating solution during the formation of skin layers in the membrane to cause the microphases separation with the increase in proportion of water in the polymer solution, whereupon the surfactants are absorbed on the surfaces of the resultant polymer-rich micro-phases or polymer-lean micro-phases to assure the stable advance of the micro-phase separation. As a result, as the solvent substitution with the coagulating liquid is advanced, the polyvinylidene fluoride type resin precipitates to form skin layers having a sharp pore diameter distribution. Thus, a hollow filament porous membrane having a high water permeability can be produced. In the above-mentioned case, the larger the amount of surfactants in said solution, the faster the water penetrates into said solution to facilitate the phase separation. However, when the amount of surfactants exceeds that of the polymer, the spinning solution becomes instable and is apt to undergo gelation and solidification, leading to various disadvantages. Therefore, the surfactants are usually employed in an amount of 0.5 to 30% by weight based on the total weight of spinning solution.

It is preferred that the resin concentration of a polyvinylidene fluoride type resin solution or a spinning solution for producing a membrane be within the range of 11 to 30 wt%. When the resin concentration is less than 11% by weight, difficulties are encountered in producing a hollow filament. More specifically, the viscosity of the spinning solution is so low that it is difficult to keep the hollow filament in an annular shape, and the filament contracts markedly because of the large degree of desolvation of the time of gelation leading to the formation of pinholes and wrinkling on the external surface of the hollow filament. Furthermore, because of the increase in the solvent concentration of the internal coagulating liquid, a thick internal skin layer is formed, leading to a poor water permeability. Therefore, as described above, it is preferred that the resin concentration of the spinning solution be 11 to 30 wt %, more preferably 15 to 25 wt %, still more preferably 17.5 to 22.5 wt %. In the case of the resin concentration exceeding 30 wt %, the resulting microfilter is low in porosity and very poor in water permeability, resulting in being useless in a practical sense.

It is preferred that the proportion of the surfactant(s) (total amount) relative to the spinning solution membrane be, as mentioned above, 0.5 to 30 wt %, more preferably 5 to 20 wt %. Furthermore, it is preferred that the amount of the surfactant(s) in the spinning solution be smaller, preferably by 1 wt % or more, than the amount of the resin employed. When the amount of the surfactant(s) exceeds the amount of the resin, the spinning solution becomes instable and is apt to be easily denatured, and, in addition, the maximum lengths of macrovoids in the support layer of the resulting membrane exceed 80% of the membrane thickness and Up pores are progressively formed in the support layer with a porosity of 85% or more, with the result that the membrane is poor in mechanical strength and burst strength and has many disadvantages as described above.

It is preferred that the temperature of the spinning solution for producing the membrane be in the range of from 20° to 70° C. and that the temperatures of both the internal and the external coagulating liquids be 20° C. or above. When the temperature of the spinning solution is higher than 70° C., the solvent employed therein fast evaporates and, hence, the phase separation of the spinning solution takes place too fast to continue the spinning operation for a long time. When the temperature of the spinning solution is lower than 20° C., a hollow filament porous membrane having a good structure cannot be obtained. The temperature of the spinning solution has only to be raised to a proper temperature just before the start of preparing a membrane.

Any non-solvent of polyvinylidene fluoride type resin may be used as the coagulating liquid. Examples of such non-solvents include water, alcohols such as methanol and ethanol, ethers, dioxane and mixtures of two or more kinds of non-solvents such as acetone/water and alcohol/water. Water is particularly preferred because it is the most inexpensive non-solvent and can be used in large amount.

When the membrane is prepared by means of an annular nozzle for producing a hollow filament, two different coagulating liquids may be respectively employed as the internal and the external coagulating liquids. Water and alcohols, such as methanol, may be used for such coagulating liquids.

In spinning a hollow filament, where the "running-in-air distance" (a distance between the tip of the spinning nozzle and the surface of the external coagulating bath) is long, the coagulation of the external surface of the membrane takes a long time and, hence, the phase separation is allowed to progress with enough time, so that large pores are formed in the external skin layer, leading to a high water permeability.

Where a long running-in-air distance is employed, the head difference should be increased for keeping the resulting hollow filament in an annular shape. In this case the extrusion pressure for the internal coagulating liquid should be increased.

An increase in the amount of the extrudate leads to a thicker membrane of the resulting hollow filament, resulting in a low permeability of the membrane.

The spinning rate depends substantially on the amount of the extrudate. An increase in the spinning rate leads to a small filament diameter, so that the water permeability of the resulting membrane increases.

It is preferred that both the internal and the external coagulating liquids have substantially the same temperature. When the temperature of the external coagulating liquid is low, as compared with that of the internal coagulating liquid, a membrane having an unsymmetrical porous structure with a thicker internal skin layer and a thinner external skin layer is formed with a lowered water permeability. On the other hand, when the temperature of the external coagulating liquid is as high as the internal coagulating liquid, the external skin layer of the resulting membrane is thick and the water permeability of the membrane is also decreased.

However, various other factors such as viscosity of the spinning solution, diameter of the spinning nozzle, and desirable membrane thickness are complicatedly involved in the spinning conditions for a hollow filament. Therefore, it is next to impossible to clarify every relationship between the above-mentioned factors.

Various conditions of spinning a hollow filament have hereinbefore been described. Spinning, with the above desirable characteristics, may be achieved as follows. A solvent for a polymer, at least one kind of surfactant, and optionally a dispersing solvent medium are mixed by stirring at about 60° C. to obtain a homogeneous solution. The resultant spinning solution, after homogenized in a warm storage tank that is gently and continually stirred for approximately an additional one hour while its temperature is kept at about 60° C. Thereafter, in order to remove bubbles generated in the spinning solution by stirring, the storage tank containing the spinning solution is evacuated to a pressure of about 100 mmHg, the pressure reducing value is closed, and the solution is allowed to stand. If the residual bubbles are still found in the spinning solution, the storage tank containing the spinning solution is again evacuated to a pressure of about 100 mmHg and the pressure-reducing valve is immediately closed, and thereafter the solution is again allowed to stand until the absence of bubbles is confirmed. This operation is called "deaeration".

The spinning solution, after deaeration, is pressured to 1 to 2 kg/cm$^2$ with air fed into a pipe connected to a spinning nozzle. The liquid-feeding pipe is also kept at about 60° C. to keep the temperature of the spinning solution constant. Between the storage tank containing the spinning solution and the hollow filament nozzle, a gear pump is installed so that the spinning solution can always be extruded from the nozzle at a constant rate predetermined by the desired filament diameter, membrane thickness and the like, thereby enabling an improvement in uniformity of the filament diameter of the hollow filament. The annular nozzle for spinning a hollow filament has an outlet for extruding the spinning solution and an outlet for extruding the internal coagulating liquid, both the outlets being warmed to maintain the temperature of the spinning solution. As described above, a non-solvent for a polyvinylidene fluoride type resin is used as the internal coagulating liquid. Purified non-solvents are especially favored. Therefore, the non-solvent is advantageously used at a constant temperature above about 20° C. after it is filtered through an ultrafiltration membrane and then deaerated. The use of a non-solvent which is not subjected to deaeration leads to bubble-clogging of the spinning nozzle, resulting in the formation of hollow filaments having varied internal and external diameters and pinholes of 10 μm or more in diameter formed in the membrane.

The spinning solution is extruded from the hollow filament spinning nozzle into the external coagulating liquid simultaneously with the extrusion of the internal coagulating liquid. The distance between the tip of the spinning nozzle and the surface of the external coagulating liquid may be either zero or more than zero, and is preferably within the range of from 0 to 20 cm. The internal and external diameters of the hollow filament formed depend on the size of the hollow filament spinning nozzle and the extruding pressure for the internal coagulating liquid. The extruding pressure of the coagulating liquid can be adjusted by means of a gear pump, a piston pump or the like.

The spinning solution extruded into the external coagulating liquid gels with desolvation and is formed into a hollow shape. For this reason, it is preferred that a external coagulating liquid tank be large enough to allow the spinning solution to gel. Emerging from the external coagulating liquid tank, the filament is passed through a first rinsing bath to a first rolls. In the first rinsing bath, the desolvation of the hollow filament proceeds and the gelation is completed. For this reason, the first rinsing bath is desired to have a higher water temperature, preferably a temperature of 40° C. or more. The first rolls consist of two or more large rolls capable of taking up hollow filaments at a constant rate. After passing through the first rolls, the hollow filament is reeled up by a wind-up machine. The hollow filament reeled up by the wind-up machine is bundled, followed by cutting the bundles and the removal of the internal coagulating liquid from the filament. Thereafter, the hollow filament is washed from both the internal and external sides of the filament to compulsorily remove the solvent contained therein. In order to improve the heat resistance, the solvent-removed hollow filament is then heat-treated at 120° C. under a pressure of steam for about one hour. A heat treatment carried out at 135° C. or above is undesirable because the fluidity of the polymer increases, leading to the crushing of the pores.

According to the present invention, as described above, one can produce hollow filament microfilters which have a high performance and can withstand repeated drying operations. The term "repeated drying operations" is used herein to mean the following repeated process comprising alternate drying and wetting procedures. The drying procedure comprises the following steps of: cutting the water-containing hollow filament obtained by the foregoing process to a predetermined length; placing the resultant hollow filament vertically to the floor to remove the water retained therein; passing air whose temperature is 30°-50° C. and whose relative humidity is 50% or less through the hollow filament, to reduce the amount of the water retained therein to 10% or less of the amount of water retained after the stage preceding to this step; and vacuum drying the filament by allowing it to stand at 100 mmHg or less for twenty-four hours in a vacuum dryer. The hollow filament thus dried is again subjected to wetting with water (wetting procedure).

In the course of the above-mentioned repeated drying, when a porous membrane containing 10% or more of water in the porous structure thereof is vacuum-dried under a pressure of 100 mmHg or less, the membrane is liable to be damaged in the porous structure because of rapid evaporation and boiling of the water contained in the structure, leading to the crushing of the pores in the membrane.

The hollow filament microfilter formed from a polyvinylidene fluoride type resin, according to the present invention, does not substantially suffer from the shrinkage of the membrane structure and the crushing of the pores in the membrane during the repeated drying. Therefore it is possible to hold the water permeability change to 30% from the time the repeated drying process begins and ends.

To the contrary, when a phydrophilic substance such as cellulose acetate is used as the starting material, the resulting membrane swells greatly in the wetting stage, resulting in the water permeability of the membrane being lowered by 50% or more by the above-mentioned drying producure. Accordingly, the cellulose acetate membrane can be dried only by means of specific methods such as freeze-drying and drying after substituting of the water with glycerin. Therefore, in using the cellulose acetate membrane, not only special attention is required to be paid so as not to dry the membrane but also additional operations such as addition of a germicide to prevent the propagation of fungi are required since used membranes should be preserved in a wetted state.

By contrast, in the case of the polyvinylidene fluoride type resin hollow filament microfilter, according to the present invention, since the material thereof is water-repellent and the membrane does not greatly shrink during the course of wet-to-dry change, it is possible to hold below 30% the water permeability change between the time a repeated drying operation begins and ends. Instead of vacuum drying the microfilter a method may be used in which the water content of the microfilter is reduced by warm air at 30° to 50° C. to 1% or less of the water content in the initial wet state (the state of the porous membrane containing water at a full content, which state is obtained after water is allowed to drop spontaneously. In short any of the following methods are acceptable vacuum drying, warm air drying, spontaneous drying, and freeze-drying as far as they enable the water content of the membrane to be reduced to 5% or less. In this sense, the polyvinylidene fluoride type resin hollow filament microfilter is easy to handle.

As described above, according to the present invention, a screen type hollow filament microfilter is produced which has a high water permeability and a high porosity, and which comprises surface skin layers having pores of a diameter adjustable as desired in the porous membrane, said pores and a support layer. The surface skin layers have an average effective pore diameter ($2\bar{r}$) of 0.05 to 1.0 μm, the range of which is broad.

BRIEF DESCRIPTION OF THE DRAWINGS

FIG. 3-(1) is a scanning type electron microscopic photograph (×12000 magnification) showing Cp pores on the surface of macrovoids in a polyvinylidene fluoride type resin hollow filament microfilter according to the present invention.

FIG. 3-(2) is a scanning type electron microscopic photograph (×1200 magnification) showing skin pores in the external surface skin layer of a polyvinylidene fluoride type resin hollow filament microfilter according to the present invention.

PREFERRED EMBODIMENTS OF THE INVENTION

The present invention will now be illustrated in more detail by the following Examples that should not be construed as limiting the scope of the invention.

EXAMPLE 1

Kynar [tradename of a polyvinylidene fluoride type resin (hereinafter abbreviated as "PVDF") manufactured by Pennwalt Company, U.S.A.], dimethylacetamide (hereinafter abbreviated as "DMAc") as the solvent, the two surfactants, namely, a polyethylene glycol having an average molecular weight of 200 (hereinafter abbreviated as "PEG200") as a first surfactant and Tween 80 (tradename of a polyoxyethylene sorbitan monooleate manufactured by Kao Altas Co., Ltd.) as a second surfactant were mixed to obtain a homogeneous solution. The solution was heated up to 60° C. and then extruded, by means of a gear pump, from an annular hollow fiber spinning nozzle into 70° C. warm water which served as the external coagulating liquid, while using 70° C. warm water as the internal coagulating liquid. The properties of the hollow fibers thus obtained are shown together with the spinning conditions in Table 2. The water permeability of every hollow fiber was examined after the hollow fiber was subjected to replacement of water with methanol.

TABLE 2

| No. | PVDF*1 (wt %) | PEG*2 (wt %) | Tween 80*4 (ml) | I.D. (mm) | O.D. (mm) | Average Effective Pore Diameter ($2\bar{r}$) (μm) | $2\bar{r}_s$ (μm) | $2\bar{r}_a$ (μm) | $\bar{r}_a/\bar{r}_s$ | Pr (%) | J*3 (m³/m² · day · atm) | Voids | Proportion*6 (%) | Burst Strength (kg/cm²) |
|---|---|---|---|---|---|---|---|---|---|---|---|---|---|---|
| 1*5 | 22.5 | 0 | 0 | 1.25 | 1.71 | 0 | 0 | 3.5 | — | 61.5 | 0 | not present | 5 | 22.0 |
| 2 | 22.5 | 10 | 0 | 1.29 | 1.75 | 0.10 | 0.10 | 2.0 | 20 | 76.0 | 8.3 | present | 30 | 12.0 |
| 3 | 22.5 | 20 | 0 | 1.30 | 1.76 | 0.10 | 0.10 | 2.0 | 20 | 79.0 | 9.0 | present | 55 | 10.0 |
| 4 | 22.5 | 10 | 1.0 | 1.29 | 1.75 | 0.11 | 0.10 | 2.5 | 25 | 79.0 | 0.0 | present | 65 | 11.2 |

*1PVDF: the polyvinylidene fluoride type resin (Kynar) content in weight percentage
*2PEG: the polyethylene glycol content in weight percentage, said polyethylene glycol having an average molecular weight of 200
*3J: water permeability
*4The amount of the surfactant incorporated is expressed in terms of ml per 100 g of the material solution.
*5No. 1 indicates a comparative example.
*6The division (%) of the length in major axial direction of the largest of the macrovoids seen in the cross section of the hollow fiber by the membrane thickness
*7The spinning rate was 10 m/min.

Figure 1:
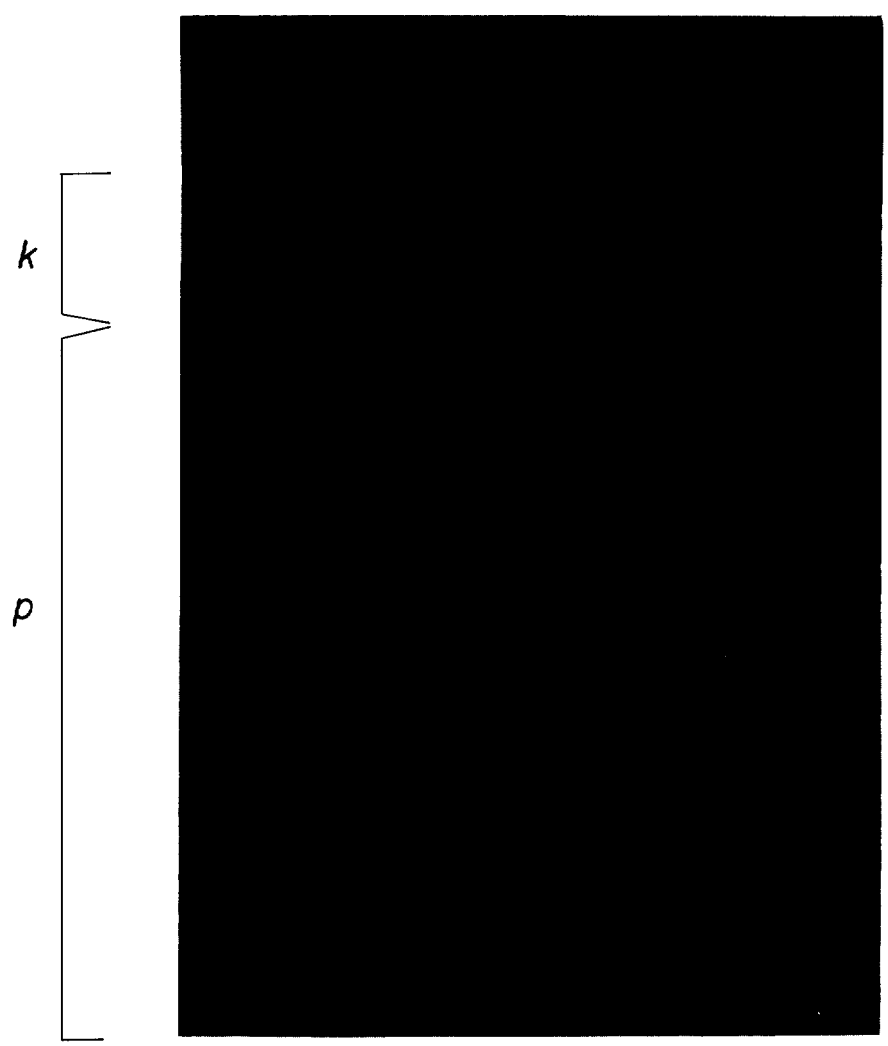
FIG. 1 is a scanning type electron microscopic photograph (×3600 magnification) of thick skin and support layers of a hollow filament porous membrane obtained by spinning a 22.5 wt % solution of a polyvinylidene fluoride type resin dissolved in dimethylacetamide by using water as internal and external coagulating liquids.
Figure 2:
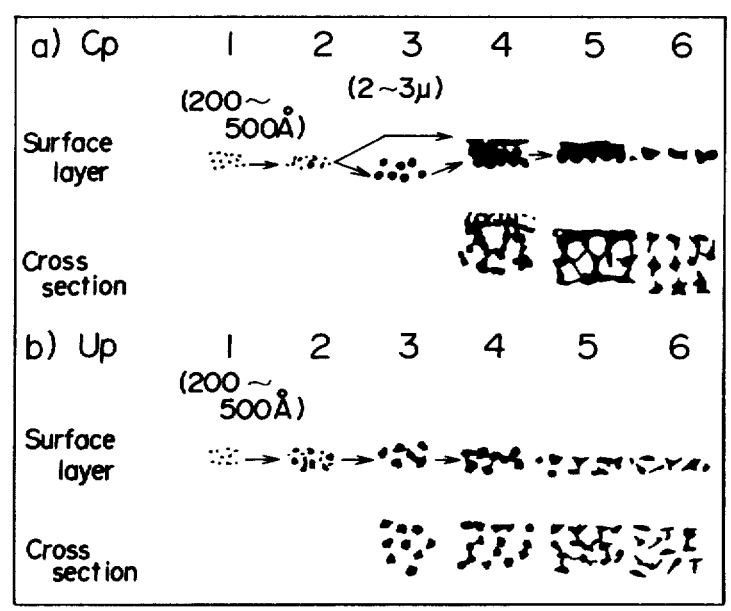
FIG. 2 is a schematic diagram demonstrating the membrane-forming mechanism of polymer porous membrane by illustrating separately the Cp pore formation and the Up pore formation.
Figure 4:
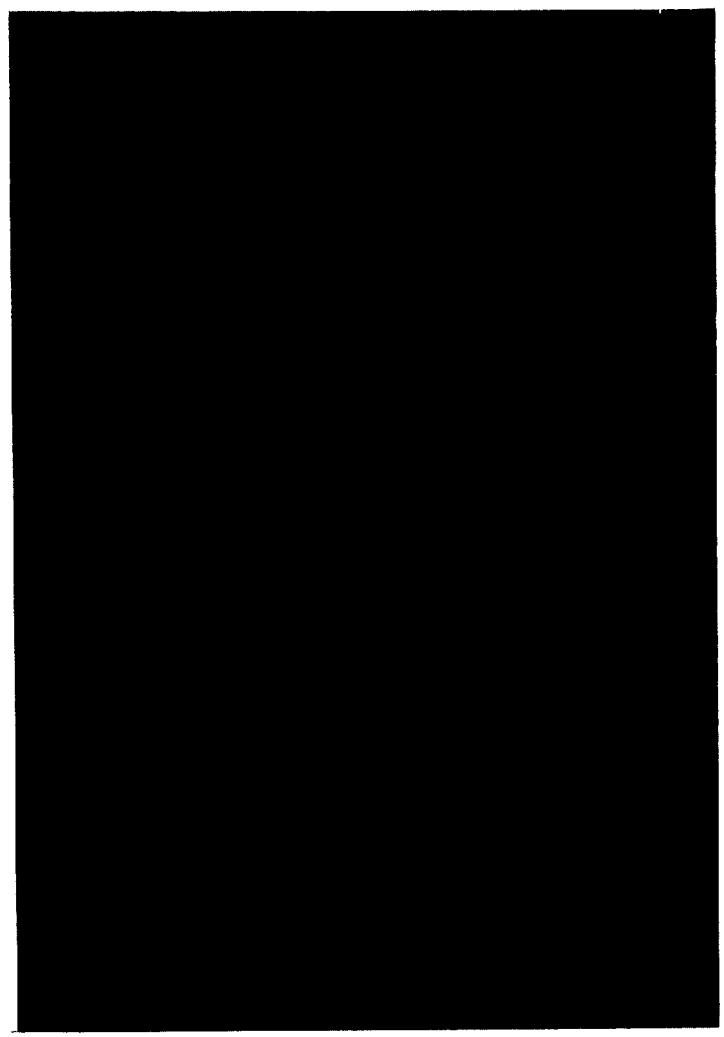
FIG. 4 is a scanning type electron microscopic photograph (×420 magnification) of a freeze-broken section of a polyvinylidene fluoride type resin hollow filament microfilter according to the present invention.

FIG. 5-(1) and 5-(2) are scanning type electron microscopic photographs (×1200 magnification) showing uniform macropores appearing in the support layer as shown in FIG. 4.

Figure 6:
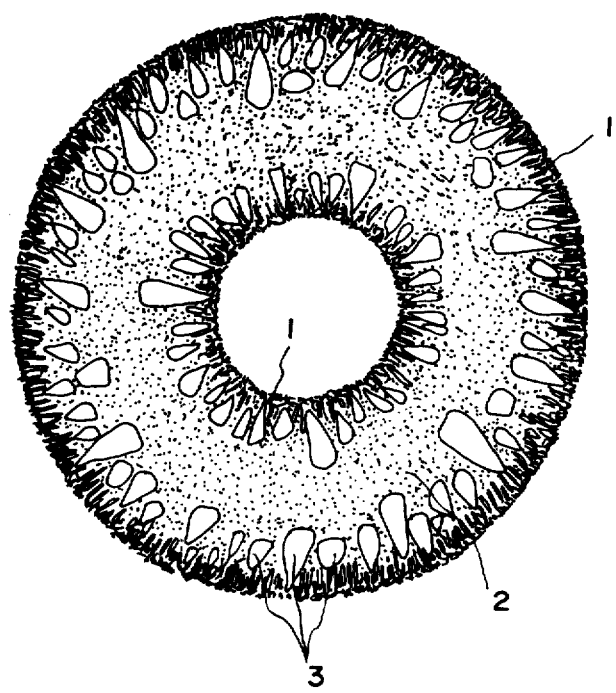

FIG. 6 is a schematic diagram of the cross-section of a polyvinylidene fluoride type resin hollow filament microfilter according to the present invention.

Figure 7:
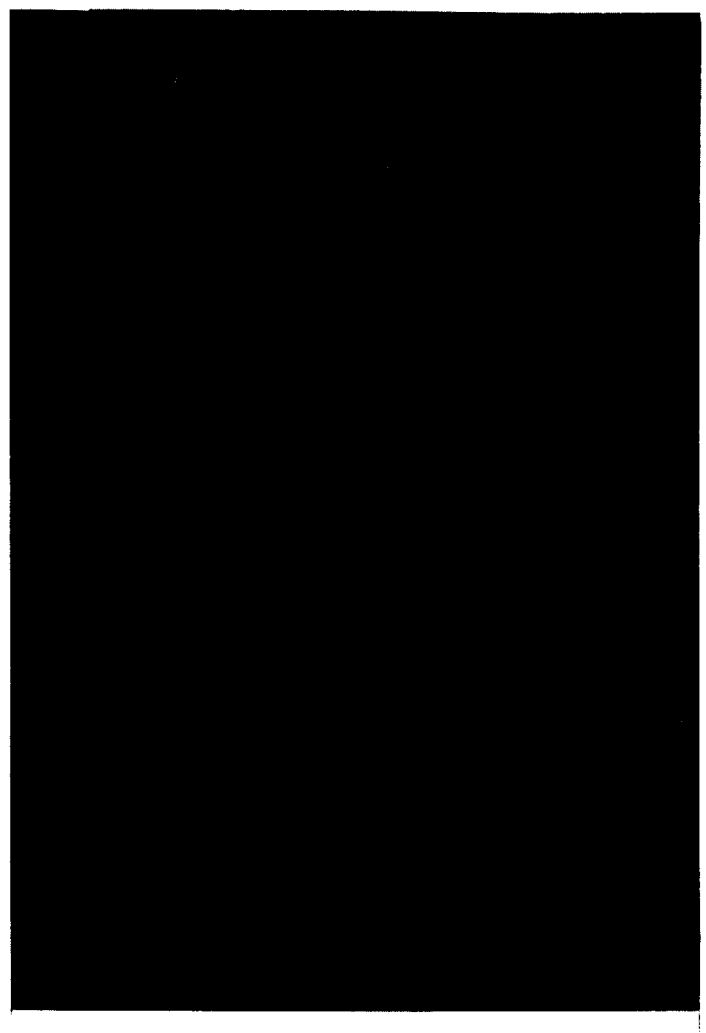

FIG. 7 is a scanning type electron microscopic photograph (×140 magnification) of the freeze-broken section of a polyvinylidene fluoride type resin hollow filament microfilter according to the present invention. This photograph shows that the macrovoid layers of this hollow filament microfilter are present on both the sides of the hollow filament, and a uniform support layer is present around the center of the hollow filament.

Figure 8:
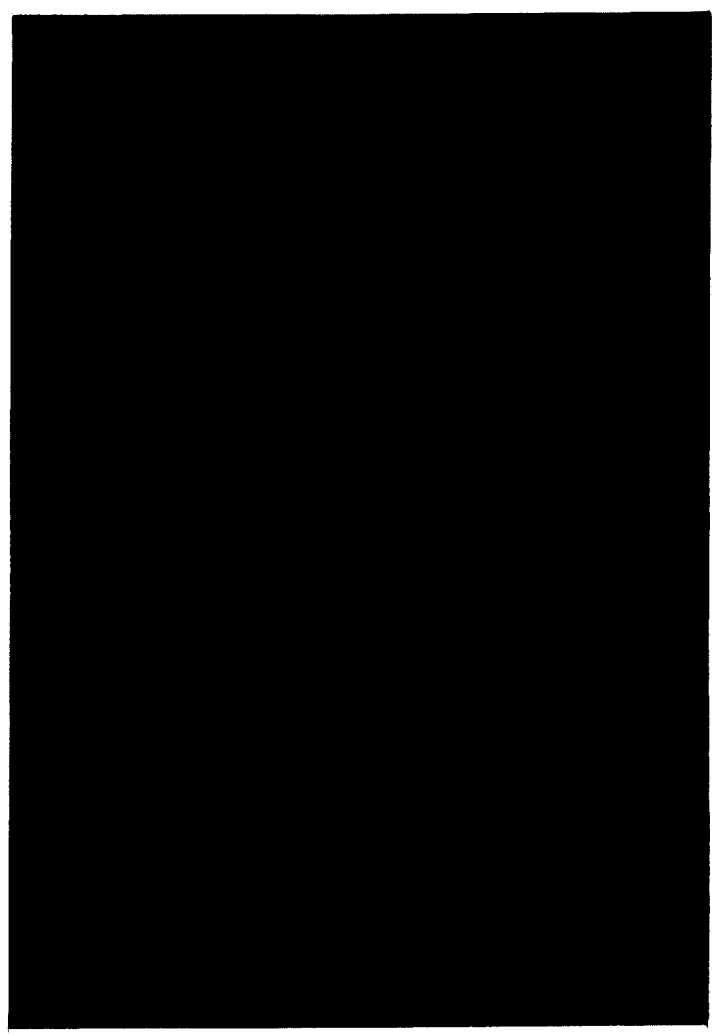

FIG. 8 is a scanning type electron microscopic photograph (×4200 magnification) showing Cp pores of the support layer exposed on the surface of microvoids in a polyvinylidene fluoride type resin hollow filament microfilter according to the present invention. This photograph demonstrates that the macropores present in the support layer are uniform and round Cp pores.

EXAMPLE 2

A polyvinylidene fluoride type resin (Kynar), DMAc as the solvent, and an additive which was a polypropylene glycol having an average molecular weight of 3000 (hereinafter abbreviated as PPG-3000) were mixed in varied proportions to obtain mixtures, to each of which Tween 80 was then added in an amount of 1 ml per 100 g of each mixture to obtain a homogeneous solution. The solution was heated to 60° C. and then extruded, by means of a gear pump, from an annular hollow fiber spinning nozzle into warm water which served as the external coagulating liquid, while using warm water as the internal coagulating liquid.

The temperatures of the internal and the external coagulation liquids were both 70° C.; the running-in-air distance was 0 cm; the rate at which the spinning solution was extruded was 20 cc per minute; and the head difference was 20 cm.

The results obtained are shown in Table 3. In No. 7 in Table 3 are shown the properties of a sample obtained by melt-spinning a polyvinylidene fluoride type resin (Kynar) at a spinning temperature of 260° C. at a spinning rate of 600 m/min, and stretching the resulting hollow filaments under ordinary temperature and pressure at a stretching proportion of 100%, followed by heat-treatment at 180° C.

Note:
stretching proportion =

$$\frac{\left(\begin{array}{c}\text{length of}\\\text{hollow filament}\\\text{after stretching}\end{array}\right) - \left(\begin{array}{c}\text{length of}\\\text{hollow filament}\\\text{prior to stretching}\end{array}\right)}{(\text{length of hollow filament prior to stretching})} \times 100$$

distance was 0 cm; and the head difference was 20 cm. The results obtained are shown in Table 4.

TABLE 4

| No. | Solvent | I.D. (mm) | O.D. (mm) | $2\bar{r}$ (μm) | $2\bar{r}_s$ (μm) | $2\bar{r}_a$ (μm) | $\bar{r}_a/\bar{r}_s$ | Pr (%) | J (m³/m² · day · atm) | Voids | Proportion (%) | Burst Strength (kg/cm²) |
|---|---|---|---|---|---|---|---|---|---|---|---|---|
| 1 | DMAc | 1.30 | 1.75 | 0.28 | 0.20 | 1.1 | 5.5 | 76 | 70 | present | 29 | 8 |
| 2 | NMP*[1] | 1.32 | 1.75 | 0.28 | 0.25 | 1.5 | 6.0 | 77 | 70 | present | 25 | 9 |
| 3 | Tetramethylurea | 1.29 | 1.71 | 0.28 | 0.25 | 2.0 | 8.0 | 77 | 70 | present | 22 | 8 |

*[1]NMP: N—methylpyrrolidone

EXAMPLE 4

Solutions were prepared from a polyvinylidene fluoride type resin (Kynar), a solvent (DMAc), and an additive (PPG 3000) with their proportions being varied. To 100 g of the resulting solutions thus obtained was added 1 ml of Tween 80 to obtain a homogeneous solution. Each solution was then heated to 50° C. and extruded, by means of a gear pump, from an annular hollow filament spinning nozzle into warm water. The temperatures of the internal and the external coagulating liquids

TABLE 3

| No. | PVDF (wt %) | PPG (wt %) | I.D. (mm) | O.D. (mm) | Membrane Thickness (mm) | $2\bar{r}$ (μm) | $2\bar{r}_s$ (μm) | $2\bar{r}_a$ (μm) | $\bar{r}_a/\bar{r}_s$ | Pr (%) | J (m³/m² · day · atm) | Voids | Proportion (%) | Burst Strength (kg/cm²) |
|---|---|---|---|---|---|---|---|---|---|---|---|---|---|---|
| 1 | 17.5 | 10.0 | 1.27 | 1.75 | 0.24 | 0.42 | 0.20 | 2.0 | 10 | 78.0 | 150 | present | 36 | 7.5 |
| 2 | 20.0 | 10.0 | 1.18 | 1.62 | 0.22 | 0.28 | 0.25 | 1.2 | 4.8 | 77.0 | 70 | present | 29 | 8 |
| 3 | 22.5 | 10.0 | 1.36 | 1.90 | 0.27 | 0.30 | 0.25 | 1.3 | 5.2 | 76.0 | 65 | present | 30 | 9 |
| 4 | 25.0 | 10.0 | 1.27 | 1.93 | 0.33 | 0.32 | 0.30 | 1.5 | 5.0 | 76.0 | 60 | present | 18 | 13 |
| 5 | 27.5 | 10.0 | 1.30 | 1.90 | 0.30 | 0.18 | 0.15 | 1.8 | 12 | 74.5 | 20 | present | 22 | 18.5 |
| 6* | 10.5 | 10.0 | 1.10 | 1.56 | 0.23 | 1.02 | 0.9 | 3.0 | 3.3 | 80.0 | 930 | present | 54 | 2 |
| 7* | — | — | 0.40 | 0.46 | 0.03 | 0.02 | 0.02 | 0.02 | 1.0 | 40.0 | 1.0 | not present | — | — |
| 8* | 10.0 | 10.0 | — | — | — | — | — | — | — | — | — | — | — | — |
| 9 | 11.0 | 10.0 | 1.00 | 1.70 | 0.35 | 0.05 | 0.05 | 5.0 | 100 | 85.0 | 2.0 | present | 50 | 2.5 |
| 10 | 13.0 | 10.0 | 1.05 | 1.70 | 0.33 | 0.10 | 0.10 | 3.0 | 30 | 79.0 | 10.0 | present | 43 | 4.0 |
| 11* | 31.0 | 10.0 | 1.10 | 1.70 | 0.30 | 0.01 | 0.01 | 3.5 | 350 | 67.0 | 0.1 | present | 7.5 | 25 |
| 12 | 11.0 | 10.0 | 1.15 | 1.72 | 0.285 | 0.08 | 0.08 | 4.3 | 53.8 | 80.0 | 8.0 | present | 29 | 2.5 |

*Nos. 6, 7, 8, and 11 indicate comparative examples. The hollow filament No. 6 was found to have pinholes and wrinkles on the interior and exterior surfaces which were rough. The hollow filament No. 7 prepared according to the melt spinning process, in which the running-in-air distance was 0 cm and a head difference of 20 cm was employed. The hollow filament 8 was found to have uneven interior and exterior surfaces having wrinkles. The hollow fiber No. 11 has a very low water permeability. In the preparation of the hollow filament No. 9 the temperature of the spinning solution was 40° C. and the temperature of warm water, which was used as both the internal and external coagulating liquids, was 50° C.

EXAMPLE 3

A polyvinylidene fluoride type resin (Kynar), a solvent therefor (DMAc, NMP or tetramethylurea) and PPG-3000 were mixed in a proportion of 20, 70 and 10 wt %, respectively, to obtain a homogeneous solution. To 100 g of the resulting solutions thus obtained was further added 1 ml of Tween 80 to obtain a homogeneous solution. Each solution was then heated to 50° C. and extruded, by means of a gear pump, from an annular hollow fiber spinning nozzle into warm water.

The temperatures of the internal and the external coagulating liquids were both 50° C.; the running-in-air were both 50° C.; the running-in-air distance was 0 cm; and the spinning rate was 10 m/min. The results obtained are shown in Table 5.

TABLE 5

| No. | PVDE (wt %) | PPG (wt %) | I.D. (mm) | O.D. (mm) | Membrane Thickness (mm) | $2\bar{r}$ (μm) | $2\bar{r}_s$ (μm) | $2\bar{r}_a$ (μm) | $\bar{r}_a/\bar{r}_s$ | Pr (%) | J (m³/m² · day · atm) | Voids | Proportion (%) | Burst Strength (kg/cm²) |
|---|---|---|---|---|---|---|---|---|---|---|---|---|---|---|
| 1 | 22.5 | 1 | 1.27 | 1.75 | 0.24 | 0.12 | 0.09 | 2.0 | 22.2 | 71.0 | 10 | present | 10 | 21 |
| 2 | 22.5 | 2 | 1.27 | 1.75 | 0.24 | 0.18 | 0.10 | 1.9 | 19.0 | 71.5 | 25 | present | 11 | 15 |
| 3 | 22.5 | 3 | 1.27 | 1.77 | 0.25 | 0.20 | 0.11 | 2.0 | 18.2 | 73.0 | 30 | present | 13 | 13 |
| 4 | 22.5 | 5 | 1.26 | 1.77 | 0.26 | 0.29 | 0.15 | 1.6 | 10.7 | 72.5 | 60 | present | 13 | 12 |
| 5 | 22.5 | 7 | 1.27 | 1.76 | 0.25 | 0.29 | 0.13 | 1.5 | 11.5 | 74.0 | 65 | present | 18 | 12 |
| 6 | 22.5 | 10 | 1.27 | 1.75 | 0.24 | 0.30 | 0.16 | 0.9 | 5.6 | 76.0 | 70 | present | 29 | 8.5 |
| 7* | 22.5 | 15 | | | | | | | | | | | | |

*No. 7 Spinning could not be effected owing to the gelation of the spinning solution. Running-in-air distance: 0 cm

EXAMPLE 5

A polyvinylidene fluoride type resin (Kynar), a solvent therefor (DMAc) and one of the surfactants listed as the additive in Table 6 were mixed in a proportion of 20, 70 and 10 wt %, respectively, to obtain a homogeneous solution. Thus, homogeneous solutions were obtained.

Each solution was spun into a hollow filament under the same conditions as in Example 4. The results obtained are shown in Table 6.

500 μm in thickness, and the membrane was, after 30 seconds, dipped into 70° C. water water. The properties of the porous membrane thus obtained are also shown in

TABLE 6

| No. | Surfactant | I.D. (mm) | O.D. (mm) | Membrane Thickness (mm) | $2\bar{r}$ (μm) | $2\bar{r}_s$ (μm) | $2\bar{r}_a$ (μm) | $\bar{r}_a/\bar{r}_s$ | Pr (%) | J (m$^3$/m$^2$ · day · atm) | Voids |
|---|---|---|---|---|---|---|---|---|---|---|---|
| 1 | ethylene glycol*[1] | 1.27 | 1.75 | 0.24 | 0.11 | 0.10 | 2.0 | 20.0 | 78.5 | 10.0 | present |
| 2 | diethylene glycol*[2] | 1.29 | 1.76 | 0.24 | 0.11 | 0.09 | 1.5 | 16.7 | 79.0 | 10.0 | present |
| 3 | PEG 200*[3] | 1.25 | 1.71 | 0.23 | 0.11 | 0.07 | 1.8 | 25.7 | 79.0 | 10.5 | present |
| 4 | PEG 3000 | 1.26 | 1.72 | 0.23 | 0.13 | 0.10 | 2.0 | 20.0 | 78.5 | 15.5 | present |
| 5 | PEG 6000 | 1.27 | 1.79 | 0.26 | 0.23 | 0.20 | 2.0 | 10.0 | 78.0 | 40.0 | present |
| 6 | propylene glycol | 1.28 | 1.77 | 0.25 | 0.20 | 0.15 | 2.5 | 6.7 | 76.5 | 30 | present |
| 7 | dipropylene glycol | 1.29 | 1.79 | 0.25 | 0.26 | 0.18 | 2.6 | 5.6 | 74.0 | 49 | present |
| 8 | tripropylene glycol | 1.21 | 1.77 | 0.28 | 0.31 | 0.18 | 2.9 | 16.1 | 75.0 | 65 | present |
| 9 | PPG 1000 | 1.24 | 1.72 | 0.24 | 0.29 | 0.20 | 3.0 | 15.0 | 78.5 | 70 | present |
| 10 | PPG 2000 | 1.27 | 1.75 | 0.24 | 0.30 | 0.21 | 2.5 | 11.9 | 76.0 | 70 | present |
| 11 | PPG 3000 | 1.27 | 1.76 | 0.25 | 0.30 | 0.28 | 2.8 | 10.0 | 76.0 | 70 | present |
| 12 | PPG 4000 | 1.28 | 1.77 | 0.25 | 0.36 | 0.30 | 3.0 | 10.0 | 79.0 | 105 | present |
| 13 | Nonion S-2 | 1.24 | 1.71 | 0.24 | 0.18 | 0.10 | 3.0 | 30.0 | 74.0 | 25 | present |
| 14 | Nonion S-207 | 1.23 | 1.77 | 0.27 | 0.16 | 0.09 | 2.5 | 27.8 | 74.5 | 19 | present |
| 15 | Nonion K-204 | 1.25 | 1.76 | 0.26 | 0.23 | 0.10 | 2.1 | 21.0 | 79.0 | 40 | present |
| 16 | Nonion LP-20R | 1.25 | 1.77 | 0.26 | 0.28 | 0.15 | 2.3 | 15.3 | 78.0 | 60 | present |
| 17 | Emulgen 903 | 1.26 | 1.79 | 0.27 | 0.29 | 0.10 | 2.4 | 24.0 | 76.0 | 63 | present |
| 18 | Anon BF | 1.27 | 1.80 | 0.27 | 0.12 | 0.05 | 1.0 | 20.0 | 76.0 | 10 | present |

*[1,2&3] In the preparation of the hollow filaments Nos. 1, 2, and 3, the amount of each surfactant added was exceptionally 20 wt %. As for the other hollow filaments, the amount of each surfactant was 10 wt %.

EXAMPLE 6

A polyvinylidene fluoride type resin (Kynar), a solvent therefor (DMAc) and an additive (PPG 3000) were mixed in a proportion of 20, 70, and 10 wt%, respectively, to effect dissolution. To 100 g of the resulting solution was added 1 ml of Tween 80 to obtain a homogeneous solution. The solution was then heated to 60° C., and extruded, by means of a gear pump at a rate of 17 to 25 ml/min, from an annular hollow filament spinning nozzle into warm water, the distance between the tip of the annular nozzle and the surface of the external coagulating liquid (running-in-air distance) being varied.

The temperatures of the internal and the external coagulating liquids were both 70° C.; and the spinning rate was 10 m/min. The results obtained are shown in Table 7. Furthermore, a spinning solution having the same composition as mentioned above was cast with a doctor blade onto a glass plate to form a membrane of 500 μm in thickness, and the membrane was, after 30 seconds, dipped into 70° C. water water. The properties of the porous membrane thus obtained are also shown in Table 7. The flat membrane thus obtained does not have a homogeneous support layer like that found in the hollow filament, and the electron microscopic photograph of the surface of the membrane showed that the membrane contains Up pores all over the surface.

TABLE 7

| No. | Running-in-Air Distance (cm) | I.D. (mm) | O.D. (mm) | Membrane Thickness (mm) | $2\bar{r}$ (μm) | $2\bar{r}_s$ (μm) | $2\bar{r}_a$ (μm) | $\bar{r}_a/\bar{r}_s$ | Pr (%) | J (m$^3$/m$^2$ · day · atm) | Voids |
|---|---|---|---|---|---|---|---|---|---|---|---|
| 1 | 0 | 1.17 | 1.75 | 0.29 | 0.33 | 0.3 | 1.2 | 4.0 | 76.5 | 70 | present |
| 2 | 1 | 1.22 | 1.74 | 0.26 | 0.45 | 0.35 | 1.5 | 4.3 | 77.0 | 150 | present |
| 3 | 3 | 1.22 | 1.70 | 0.24 | 0.55 | 0.4 | 1.6 | 4.0 | 78.0 | 250 | present |
| 4 | 5 | 1.21 | 1.65 | 0.22 | 0.62 | 0.5 | 2.0 | 4.0 | 78.5 | 350 | present |
| 5 | 7 | 1.18 | 1.60 | 0.21 | 0.46 | 0.4 | 1.6 | 4.0 | 78.0 | 200 | present |
| 6 | 9 | 1.05 | 1.55 | 0.20 | 0.31 | 0.3 | 1.2 | 4.0 | 80.0 | 100 | present |
| 7*[1] | — | — | — | 0.22 | 0.73 | 0.50 | 2.0 | 4.0 | 72.7 | 450 | present |
| 8*[2] | 5 | 1.26 | 1.70 | 0.22 | 0.98 | 0.90 | 5.5 | 6.1 | 80.0 | 400 | present |
| 9*[2] | 0 | 1.20 | 1.80 | 0.30 | 0.90 | 0.70 | 8.0 | 11.4 | 79.0 | 300 | present |
| 10*[2] | 0 | 1.20 | 1.80 | 0.30 | 0.50 | 0.35 | 9.0 | 25.7 | 79.0 | 200 | present |

*[1] No. 7 indicates the flat membrane
*[2] Nos. 8, 9, and 10 indicate the hollow filaments prepared using PPG4000 as the surfactant instead of PPG3000.

EXAMPLE 7

A polyvinylidene fluoride type resin (kynar), a solvent therefor (DMAc), and a surfactant (PPG 3000) were mixed in a proportion of 20, 70 and 10 wt%, respectively, and to 100 ml of the resulting mixture was added 1 ml of Tween 80 to obtain a homogeneous solution. The solution was then extruded, by means of a gear pump, from an annular hollow filament spinning nozzle into an external coagulating liquid which was varied, while using an internal coagulating liquid which was also varied. The temperature of the spinning solution was 60° C.; and the spinning rate was 10 m/min. The results obtained are shown in Table 8.

TABLE 8

| No. | CBT$_1$ (°C.) | CBT$_2$ (°C.) | I.D. (mm) | O.D. (mm) | Membrane Thickness (mm) | $2\bar{r}$ (μm) | $2\bar{r}_s$ (μm) | $2\bar{r}_a$ (μm) | $\bar{r}_a/\bar{r}_s$ | Pr (%) | J (m$^3$/m$^2$ · day · atm) | Voids | Burst Strength (kg/cm$^2$) |
|---|---|---|---|---|---|---|---|---|---|---|---|---|---|
| 1 | 20 | 20 | 1.40 | 1.93 | 0.27 | 0.15 | 0.12 | 2.0 | 16.7 | 72.0 | 75 | present | 11.0 |
| 2 | 30 | 30 | 1.30 | 1.89 | 0.30 | 0.17 | 0.15 | 2.5 | 16.7 | 74.0 | 78 | present | 10.0 |
| 3 | 40 | 40 | 1.36 | 1.89 | 0.27 | 0.24 | 0.20 | 1.9 | 9.5 | 75.5 | 40 | present | 9.0 |

TABLE 8-continued

| No. | CBT$_1$ (°C.) | CBT$_2$ (°C.) | I.D. (mm) | O.D. (mm) | Membrane Thickness (mm) | $2\bar{r}$ ($\mu$m) | $2\bar{r}_s$ ($\mu$m) | $2\bar{r}_a$ ($\mu$m) | $\bar{r}_a/\bar{r}_s$ | Pr (%) | J (m$^3$/m$^2$ · day · atm) | Voids | Burst Strength (kg/cm$^2$) |
|---|---|---|---|---|---|---|---|---|---|---|---|---|---|
| 4 | 50 | 50 | 1.34 | 1.85 | 0.26 | 0.30 | 0.18 | 1.0 | 5.6 | 75.0 | 65 | present | 9.0 |
| 5 | 60 | 60 | 1.30 | 1.75 | 0.22 | 0.28 | 0.20 | 1.2 | 6.0 | 76.0 | 70 | present | 9.5 |
| 6 | 60 | 40 | 1.36 | 1.95 | 0.30 | 0.31 | 0.20 | 1.2 | 6.0 | 76.0 | 60 | present | 9.0 |

CBT$_1$ denotes the temperature of the external coagulating liquid
CBT$_2$ denotes the temperature of the internal coagulating liquid

EXAMPLE 8

Several pieces of the hollow filament No. 2 mentioned in Table 2 in Example 2 were cut to 50 cm. Water retained in pieces of the hollow filament porous membrane was swished off, and the pieces of the hollow filament porous membrane were respectively dried with dried air having a relative humidity of 20% at temperatures of 50° C., 40° C. and 25° C. to a water content of 10% or less, followed by one day's reduced-pressure drying in a vacuum dryer and replacement of the remaining water with methanol. The water permeabilities of the resulting pieces of the hollow filament porous membrane was examined to find decreases in a water permeability of 15, 10 and 7%, respectively. On the other hand, when the hollow filament porous membrane was subjected directly to vacuum drying even without switching water off, the decrease in water permeability was 95%. When the hollow filament porous membrane was subjected to vacuum drying after it had a water content of 50%, the decrease in water permeability was 80%.

On the other hand, cellulose diacetate having an acetylation degree of 54%, acetone, methanol, cyclohexanol and CaCl$_2$.2H$_2$O were mixed to form a homogeneous solution, which was then spun into water according to the method disclosed in British Pat. No. 1,506,785. With respect to the cellulose acetate hollow filament porous membrane, the decrease in water permeability was 50% and the strength in a dried state was very low.

EXAMPLE 9

A polyvinylidene fluoride type resin (Kynar), a solvent therefor (DMAc) and an additive (PPG 3000) were mixed in a weight proportion of 22.5, 67.5 and 10 wt%, respectively. To 100 g of the resulting solution was added 1 ml of Tween 80 to obtain a homogeneous solution. The solution was spun into hollow filaments having varied sizes under substantially the same conditions as in Example 4. The properties of the hollow filaments are shown in Table 9.

prepare a homogeneous solution. To 100 g of the solution was added 1 ml of Tween 80 to obtain a homogeneous solution. The solution was spun into a hollow filament under the same spinning conditions as in Example 2.

The hollow filament obtained had a water permeability of 20 (m$^3$/m$^2$.day.atm) and an average pore diameter of 0.18 $\mu$m. A latex of dispersed particles of 0.2 $\mu$m in size was diluted with water to form a 0.05% dispersion, which was then passed through the hollow filament. The latex particles of 0.2 $\mu$m in size was completely prevented from permeating through the hollow filament porous membrane, and the water permeability was constantly 18 (m$^3$/m$^2$.day.atm).

EXAMPLE 11

Twenty percent by weight of a polyvinylidene fluoride type resin (Kynar), sixty percent by weight of a solvent therefor (DMAc), ten percent by weight of a dispersing solvent medium (dioxane) and ten percent by weight % of Tween 80 [a surfactant (polyoxyethylene sorbitan-monooleate) manufactured by Kao Atlas Co., Ltd.] was mixed and agitated to obtain a homogeneous solution. The solution was then heated to 60° C., and spun, by means of a gear pump, into a hollow filament from an annular hollow filament spinning nozzle by using 50° C. warm water as the internal and the external coagulating liquids. The hollow filament had an external diameter of 1.75 mm, an internal diameter of 0.75 mm and a porosity of 72%.

EXAMPLE 12

Twenty percent by weight of a polyvinylidene fluoride type resin (Kynar), seventy percent by weight % of a solvent therefor (DMAc), ten percent by weight of polypropylene glycol with an average molecular weight of 3,000 as a surfactant and 1 ml per 100 g of the resulting mixture, of Tween 80 as another surfactant were mixed and agitated to obtain a homogeneous solution. The solution was heated to 60° C., and spun, by means of a gear pump, into a hollow filament from an

TABLE 9

| No. | I.D. (mm) | O.D. (mm) | Membrane Thickness (mm) | $2\bar{r}$ ($\mu$m) | $2\bar{r}_s$ ($\mu$m) | $2\bar{r}_a$ ($\mu$m) | $\bar{r}_a/\bar{r}_s$ | Pr (%) | J (m$^3$/m$^2$ · day · atm) | Burst Strength (kg/cm$^2$) | Voids |
|---|---|---|---|---|---|---|---|---|---|---|---|
| 1 | 1.27 | 1.75 | 0.24 | 0.3 | 0.16 | 0.9 | 5.6 | 76 | 70 | 9 | present |
| 2 | 1.38 | 2.33 | 0.48 | 0.35 | 0.25 | 0.9 | 3.6 | 75 | 50 | 8 | present |
| 3 | 0.75 | 1.38 | 0.315 | 0.28 | 0.18 | 0.95 | 5.3 | 75 | 80 | 18.0 | present |
| 4 | 0.15 | 0.30 | 0.08 | 0.18 | 0.14 | 1.0 | 7.1 | 75 | 80 | 22.0 | present |

EXAMPLE 10

A polyvinylidene fluoride type resin (Kynar), DMAc and PPG 3000 were mixed in a proportion of 27.5, 62.5 and 10 wt %, respectively, followed by agitation, to annular hollow filament spinning nozzle by using varied internal and external coagulating liquids. The temperatures of the internal and the external coagulating liquids were both 30° C.; and the spinning rate was 10 m/min. The results obtained are shown in Table 10.

TABLE 10

| No. | Internal Coagulating Liquid | External Coagulating Liquid | I.D. (mm) | O.D. (mm) | Membrane thickness (mm) | $2\bar{r}$ (μm) | $2\bar{r}_s$ (μm) | $2\bar{r}_a$ (μm) | $\bar{r}_a/\bar{r}_s$ | Pr (%) | J m³/m²·day·atm | Voids |
|---|---|---|---|---|---|---|---|---|---|---|---|---|
| 1 | ethanol | water | 1.25 | 1.90 | 0.325 | 0.15 | 0.13 | 1.2 | 9.23 | 72.0 | 20 | present |
| 2 | ethanol | water | 1.23 | 1.80 | 0.285 | 0.15 | 0.13 | 1.3 | 10.0 | 72.5 | 23 | present |
| 3 | ethanol/water (1/1) | water | 1.22 | 1.85 | 0.315 | 0.16 | 0.12 | 1.2 | 10.0 | 73.0 | 35 | present |
| 4 | water | methanol/water (1/1) | 1.27 | 1.85 | 0.290 | 0.16 | 0.12 | 1.2 | 10.0 | 75.0 | 32 | present |
| 5 | methanol | methanol | 1.25 | 1.80 | 0.225 | 0.12 | 0.10 | 1.1 | 11.0 | 70.0 | 12 | present |
| 6 | methanol | ethanol | 1.24 | 1.84 | 0.300 | 0.10 | 0.09 | 1.0 | 11.1 | 68.5 | 13.5 | present |
| 7 | dioxane | ethanol | 1.25 | 1.85 | 0.300 | 0.08 | 0.06 | 1.0 | 16.7 | 69.0 | 8.0 | present |
| 8 | water | water | 1.30 | 1.89 | 0.300 | 0.17 | 0.15 | 2.5 | 16.7 | 74.0 | 78 | present |

PROBABILITY OF UTILIZATION IN INDUSTRY

As described above, the polyvinylidene fluoride type resin hollow filament microfilter, according to the present invention, has a wide variety of prospective uses including the separation of emulsions, yeasts and fungi in view of the facts that it permits proteins with a molecular weight of from thousands to hundreds of thousands to pass therethrough whereas it does not permit those with a large molecular weight, such as yeasts (2 to 4 μm), fungi (1 to 2 μm) and pathogenic viruses (molecular weight: 2,400,000) to pass therethrough, that it permits albumin contained in body fluid to pass therethrough but does not permit fungi to pass therethrough, and that it permits colloidal particles to pass therethrough but does not permit emulsion particles to pass therethrough. Its specific uses at present include filters for filter type artificial kidney and separation of various fungi (e.g., filters for separation of fungi in abdomina pdropsy and viruses and final filters for liquid transfusion) and for use as a filter separation of blood plasma and hemocyte from blood and for separation-purification of pharmaceuticals.

What is claimed is:

1. A hollow filament microfilter which comprises a polyvinylidene fluoride type resin membrane having a substantially annular shape in cross-section and comprising internal and external surface skin layers and a support layer connected thereto; said skin layers being uniformly porous layers with a average pore diameter ($2\bar{r}_s$) of 0.05 to 1.0 μm, said support layers being a uniformly porous layer with an average pore diameter ($2\bar{r}_a$) of 1 to 10 μm, a relationship represented by the formula $\bar{r}_a/\bar{r}_s \geq 4$ being satisfied, said support layer having a plurality of macrovoids extending radially in the substantially annular cross-section of the resin membrane, said macrovoids each having a length of at least 10% and at most 80%, based on the thickness of the resin membrane, in the radially extending axis direction in said cross-section, said resin membrane having an average effective pore diameter ($2\bar{r}$) of 0.05 to 1.0 μm and a porosity of 60 to 85%.

2. A hollow filament microfilter according to claim 1, which has a water permeability of at least 8 m³/m²·day·atm.

3. A hollow filament microfilter according to claim 1, which has a change of up to 30% in water permeability by repeated drying operations.

4. A hollow filament microfilter according to claim 1, which has a burst strength of 2.5 kg/cm² or more.

* * * * *